(12) United States Patent  
Sagner et al.

(10) Patent No.: US 8,137,616 B2
(45) Date of Patent: Mar. 20, 2012

(54) SYSTEM FOR MULTI COLOR REAL TIME PCR

(75) Inventors: Gregor Sagner, Penzberg (DE); Ingrid Bechler, Gelting (DE); Jochen Bolte, Buerstadt (DE); Dieter Heindl, Paehl (DE); Hans-Peter Josel, Weilheim (DE); Martin Gutekunst, Eberfing (DE); Rudolf Sebl, Penzberg (DE); Christoph Mueller, Munich (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 10/549,648

(22) PCT Filed: Apr. 1, 2004

(86) PCT No.: PCT/EP2004/003457
§ 371 (c)(1),
(2), (4) Date: Sep. 15, 2005

(87) PCT Pub. No.: WO2004/087950
PCT Pub. Date: Oct. 14, 2004

(65) Prior Publication Data
US 2006/0269922 A1    Nov. 30, 2006

(30) Foreign Application Priority Data

Apr. 4, 2003   (EP) .................................... 03007458
Jul. 1, 2003    (EP) .................................... 03014929
Aug. 7, 2003   (EP) .................................... 03017561

(51) Int. Cl.
*C12Q 1/68*     (2006.01)
*G01N 15/06*    (2006.01)
*G01N 33/00*    (2006.01)
*G01N 33/48*    (2006.01)
*G01N 33/566*   (2006.01)
*C12P 19/34*    (2006.01)

(52) U.S. Cl. .......... 422/50; 422/68.1; 435/6.1; 435/91.2; 436/501

(58) Field of Classification Search ........................ None
See application file for complete search history.

(56) References Cited

U.S. PATENT DOCUMENTS
5,118,801 A    6/1992  Lizardi et al. ................... 536/27
(Continued)

FOREIGN PATENT DOCUMENTS
EP    0 640 828 A1    3/1995
(Continued)

OTHER PUBLICATIONS

Bell and Ranford-Cartwright (2002) Trends in Parasitology vol. 18 No. 8 pp. 337-342.*

(Continued)

*Primary Examiner* — Teresa E Strzelecka
(74) *Attorney, Agent, or Firm* — M. Reza Savari; Olga Kay; Charles M. Doyle

(57) ABSTRACT

The invention is directed to a system for performing multi-color real time PCT, comprising a flexible real time PCT instrument and a specific composition or reaction mixture for performing multiplex PCR: In particular, the present invention is directed to a composition or reaction mixture which comprises at least 3, preferably 4-5 and most preferably exactly 4 pairs of FRET hybridization probes. Each pair of said hybridization probes consists of a FRET donor probe carrying a FRET donor moiety and a FRET acceptor probe carrying a FRET acceptor moiety having an emission maximum between 550 and 710 nm.

4 Claims, 15 Drawing Sheets

U.S. PATENT DOCUMENTS

| | | | |
|---|---|---|---|
| 5,538,848 A | 7/1996 | Livak et al. | 435/5 |
| 5,563,588 A * | 10/1996 | Belfer | 340/907 |
| 5,750,409 A | 5/1998 | Herrmann et al. | 436/517 |
| 5,837,196 A * | 11/1998 | Pinkel et al. | 422/55 |
| 5,869,255 A | 2/1999 | Mathies et al. | 435/6 |
| 5,928,907 A | 7/1999 | Woudenberg et al. | 435/91.2 |
| 6,015,674 A | 1/2000 | Woudenberg et al. | 435/6 |
| 6,140,054 A | 10/2000 | Wittwer et al. | 435/6 |
| 6,150,107 A * | 11/2000 | Glazer et al. | 435/6 |
| 6,174,670 B1 | 1/2001 | Wittwer et al. | 435/6 |
| 6,177,247 B1 | 1/2001 | Mathies et al. | 435/6 |
| 6,197,520 B1 | 3/2001 | Wittwer et al. | 435/6 |
| 6,369,893 B1 | 4/2002 | Christel et al. | 356/417 |
| 6,870,165 B2 * | 3/2005 | Amirkhanian et al. | 250/458.1 |
| 7,081,226 B1 * | 7/2006 | Wittwer et al. | 422/68.1 |
| 2004/0014202 A1 * | 1/2004 | King et al. | 435/287.2 |

FOREIGN PATENT DOCUMENTS

| | | |
|---|---|---|
| EP | 0 747 447 B1 | 12/1996 |
| WO | 9521266 A1 | 8/1995 |
| WO | 9521266 R3 | 8/1995 |
| WO | WO 97/46707 | 12/1997 |
| WO | WO 97/46712 | 12/1997 |
| WO | WO 97/46714 | 12/1997 |
| WO | WO 98/49340 | 11/1998 |
| WO | 9960380 A1 | 11/1999 |
| WO | 0112854 A2 | 2/2001 |
| WO | 0112854 A3 | 2/2001 |
| WO | WO 02/14555 A2 | 2/2002 |
| WO | WO 2004/087950 A2 | 10/2004 |

OTHER PUBLICATIONS

Costa et al. (2001) Prenatal Diagnosis 21:85-88.*
Wittwer et al. (1997) Biotechniques vol. 22, No. 1 pp. 176-181.*
Hiratsuka et al. (2002) Clinical Biochemistry vol. 35 (1) pp. 35-40.*
Epstein et al. (2002) Analytica Chimica Acta 469: pp. 3-36.*
03 01 7561.6 App, Aug. 11, 2004, EP Search Report.
03 01 4929.8 App, Feb. 4, 2004, EP Search Report.
PCT/EP2004/003457, Oct. 13, 2004, PCT Search Report.

Bernard, P., et al, 1998, "Integrated Amplification and Detection of the C677T Point Mutation in the Methylenetetrahydrofolate Reductase Gene by Fluorescence Resonance energy Transfer and Probe Melting Curves", *Analytical Biochemistry*, 235: 101-107.
Bio-Rad, 2001, "BioRadiations", *BioRadiations*, 107: 1-31.
Glazer, A., et al, 1997"Energy-transfer fluorescent reagents for DNA analyses", *Analytical Biotechnology*.
Heid, C., et al, 1996, "Real Time Quantitative PCR", *Genome Research*, 6:986-994.
Ju, J., et al, 1995, "Design and Synthesis of Fluorescence Energy Transfer Dye-Labeled Primers and Their Application for DNA Sequencing and Analysis", *Analytical Biochemistry*, 231: 131-140.
Marras, S., et al, 2002, "Efficiencies of Fluorescence Resonance Energy Transfer and Contact-Mediated Quenching in Oligonudeotide Probes", *Nucleic Acids Research*, 30 (21): e122.
Matthews, J., et al, 1988, "Review: Analytical Strategies for the Use of DNA Probes", *Analytical Biochemistry* 169: 1-25.
Palladino, S., et al, 2002, "Real-time PCR for the rapid detection of vanA and vanB genes", *Diagnostic Microbiology and Infectious Disease*, (45): 81-84.
Roter-Gene 3000, "Four-Channel Multiplexing System", *Corbett Research*, 1-8.
Vet, J., et al, 1999, "Multiplex Detection of Four Pathogenic Retroviruses using Molecular Beacons", *Proc. Natl. Acad. Sci USA*, 96: 6394-6399.
Lee, L.G., et al., 1999, "Seven-Color, Homogeneous Detection of Six PCR Products", *BioTechniques*, 27:342-349.
Bernard, Philip S., et al., "Homogeneous Amplification and Variant Detection by Fluorescent Hybridization Probes", *Clinical Chemistry*, 46(2)147-148.
Wittwer, Carl T., et al., 2001, "Real-Time Multiplex PCR Assays", *Methods*, 25:430-442.
Takakusa, Hideo, el. al., 2003, "A Novel Design Method of Ratiometric Fluorescent Probes Based on Fluorescence Resonance Energy Transfer Switching by Spectral Overlap Integral", Chem. Eur. J., 9(7):1479-1485.

* cited by examiner

F3 = 610 nm
Without Color Compensation

With Color Compensation

F4 = 640 nm
Without Color Compensation

With Color Compensation

F5 = 670 nm
Without Color Compensation

With Color Compensation

F6 = 710 nm
Without Color Compensation

With Color Compensation 610 nm channel without color compensation 610 nm channel with color compensation 640 nm channel without color compensation 640 nm channel with color compensation 670 nm channel without color compensation 670 nm channel with color compensation 705 nm channel without color compensation 705 nm channel with color compensation

F1: 530nm (FAM)

F2: 560 nm (Hex)

F1: 530nm (FAM)

F2: 560 nm (HEX)

SEQUENCE LISTING

<160> NUMBER OF SEQ ID NOS: 13

<210> SEQ ID NO 1
<211> LENGTH: 22
<212> TYPE: DNA
<213> ORGANISM: Artificial
<220> FEATURE:
<221> NAME/KEY: misc_feature
<223> OTHER INFORMATION: Primer FactorV, forward

<400> SEQUENCE: 1
gagagacatc gcctctgggc ta                                            22

<210> SEQ ID NO 2
<211> LENGTH: 20
<212> TYPE: DNA
<213> ORGANISM: Artificial
<220> FEATURE:
<221> NAME/KEY: misc_feature
<223> OTHER INFORMATION: Primer FactorV, reverse

<400> SEQUENCE: 2
tgttatcaca ctggtgctaa                                               20

<210> SEQ ID NO 3
<211> LENGTH: 23
<212> TYPE: DNA
<213> ORGANISM: Artificial
<220> FEATURE:
<221> NAME/KEY: misc_feature
<223> OTHER INFORMATION: 3'Fluorescein labeled Hybridization Probe

<400> SEQUENCE: 3
aatacctgta ttcctcgcct gtc                                           23

<210> SEQ ID NO 4
<211> LENGTH: 36
<212> TYPE: DNA
<213> ORGANISM: Artificial
<220> FEATURE:
<221> NAME/KEY: misc_feature
<223> OTHER INFORMATION: 5' Red610 Hybridization Probe
<220> FEATURE:
<221> NAME/KEY: misc_feature
<223> OTHER INFORMATION: 5' Cy5 Hybridization Probe
<220> FEATURE:
<221> NAME/KEY: misc_feature
<223> OTHER INFORMATION: 5' Red640 Hybridization Probe
<220> FEATURE:
<221> NAME/KEY: misc_feature
<223> OTHER INFORMATION: 5' Red705 Hybridization Probe

<400> SEQUENCE: 4
agggatctgc tcttacagat tagaagtagt cctatt                             36

<210> SEQ ID NO 5
<211> LENGTH: 19
<212> TYPE: DNA
<213> ORGANISM: Artificial
<220> FEATURE:
<221> NAME/KEY: misc_feature
<223> OTHER INFORMATION: Primer forward

<400> SEQUENCE: 5
tgccttgcat tttctgctt                                                19

<210> SEQ ID NO 6

```
<211> LENGTH: 19
<212> TYPE: DNA
<213> ORGANISM: Artificial
<220> FEATURE:
<221> NAME/KEY: misc_feature
<223> OTHER INFORMATION: Primer reverse

<400> SEQUENCE: 6
gagttgggtg atacataca                                                    19

<210> SEQ ID NO 7
<211> LENGTH: 32
<212> TYPE: DNA
<213> ORGANISM: Artificial
<220> FEATURE:
<221> NAME/KEY: misc_feature
<223> OTHER INFORMATION: 3'-Fluorescein HybProbe 1

<400> SEQUENCE: 7
gaaattcttt gtttgtaata tactgctctc tc                                     32

<210> SEQ ID NO 8
<211> LENGTH: 18
<212> TYPE: DNA
<213> ORGANISM: Artificial
<220> FEATURE:
<221> NAME/KEY: misc_feature
<223> OTHER INFORMATION: 5'-Red610 HybProbe 1a

<400> SEQUENCE: 8
tgatttggtc cacgtacc                                                     18

<210> SEQ ID NO 9
<211> LENGTH: 19
<212> TYPE: DNA
<213> ORGANISM: Artificial
<220> FEATURE:
<221> NAME/KEY: misc_feature
<223> OTHER INFORMATION: 5'-Red640 HybProbe 1b

<400> SEQUENCE: 9
tgatttggtc caagtaccc                                                    19

<210> SEQ ID NO 10
<211> LENGTH: 37
<212> TYPE: DNA
<213> ORGANISM: Artificial
<220> FEATURE:
<221> NAME/KEY: misc_feature
<223> OTHER INFORMATION: 3'-Fluorescein HybProbe 2

<400> SEQUENCE: 10
gttggagacg tctgcaggta tgtattcata gactcaa                                37

<210> SEQ ID NO 11
<211> LENGTH: 20
<212> TYPE: DNA
<213> ORGANISM: Artificial
<220> FEATURE:
<221> NAME/KEY: misc_feature
<223> OTHER INFORMATION: 5'-Red705 HybProbe 2

<400> SEQUENCE: 11
atcttcaatt gttcgaggtt                                                   20

<210> SEQ ID NO 12
<211> LENGTH: 28
<212> TYPE: DNA
```

-continued

```
<213> ORGANISM: Artificial
<220> FEATURE:
<221> NAME/KEY: misc_feature
<223> OTHER INFORMATION: 3'-Fluorescein HybProbe 3

<400> SEQUENCE: 12
atttccttgg ggagaaatct cgtgccca                                    28

<210> SEQ ID NO 13
<211> LENGTH: 38
<212> TYPE: DNA
<213> ORGANISM: Artificial
<220> FEATURE:
<221> NAME/KEY: misc_feature
<223> OTHER INFORMATION: 5'-RedCy5 HybProbe 3

<400> SEQUENCE: 13
acctggtgat gaatccctta ctatttagaa taaggaac                         38
```

SYSTEM FOR MULTI COLOR REAL TIME PCR

This application claims the benefit of priority under 35 U.S.C. §119 of PCT/EP2004/003457, filed 1 Apr. 2004, EP Application No. 03017561.6 filed 7 Aug. 2003, EP Application No. 03014929.8, filed 1 Jul. 2003 and EP Application No. 03007458.7, filed 4 Apr. 2003, the contents of which are hereby incorporated by reference.

BACKGROUND OF THE INVENTION

1. Field of Invention

The present invention relates to the field of Real time PCR. In particular, the present invention is directed to a system for performing multiplex real time PCR.

2. Prior Art Background

Amplification of DNA by polymerase chain reaction (PCR) is a technique fundamental to molecular biology. Nucleic acid analysis by PCR requires sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR. See, for example, U.S. Pat. No. 6,174,670.

Monitoring fluorescence during each cycle of PCR initially involved the use of ethidium bromide. (Higuchi R, G Dollinger, P S Walsh and R. Griffith, Simultaneous amplification and detection of specific DNA sequences, Bio/Technology 10 (1992) 413-417; Higuchi R, C Fockler G Dollinger and R Watson, Kinetic PCR analysis: real time monitoring of DNA amplification reactions, Bio/Technology 11 (1993) 1026-1030). In that system fluorescence is measured once per cycle as a relative measure of product concentration. Ethidium bromide detects double stranded DNA; if template is present fluorescence intensity increases with temperature cycling. Furthermore, the cycle number where an increase in fluorescence is first detected increases inversely proportionally to the log of the initial template concentration. Other fluorescent systems have been developed that are capable of providing additional data concerning the nucleic acid concentration and sequence.

In kinetic real time PCR, the formation of PCR products is monitored in each cycle of the PCR. The amplification is usually measured in thermocyclers which have additional devices for measuring fluorescence signals during the amplification reaction.

Real Time PCR Instrumentation

Several types of real time detection thermocyclers are known in the art.

EP 0 640 828, for example discloses an apparatus for monitoring multiple nucleic acid amplification simultaneously. It is characterized in that it comprises a metal block thermal cycler, including a heat conducting member having multiple recesses formed therein in order to take up a multiwell plate such as a microtiter plate. Detection is obtained by means of a CCD camera, arranged for detecting light emitted (simultaneously) from all of said recesses. Alternatively, the use of fiber optics is suggested. Depending on the fluorescent dyes which are used and—more important—, depending on the presence of a filter wheel close to the CCD camera, the system has the capability of analyzing multiplex amplification reactions, wherein in one reaction chamber, one or more different amplicons are detected by 2 or more differently labeled hybridization probes. Yet, EP 0 640 828 does neither anticipate nor suggest, which labels or detection formates could be used for such a multiplex/multicolor approach.

U.S. Pat. No. 6,015,674 discloses an apparatus and a system for real time PCR detection and quantification, characterized in that it is capable of detecting first and second fluorescent indicators, which may be used as labels for different hybridization probes in order to detect different amplicons in the same reaction vessel. Yet, U.S. Pat. No. 6,015,674 does not disclose a system for performing multiple experiments with a higher degree of complexity.

Another typical example is the Roche Diagnostics LightCycler (Cat. No. 2 0110468). It is a fast PCR system enabling kinetic on-line PCR quantification and subsequent analysis of PCR-product melting curves. The optical system of the current LightCycler version 1.2 being commercially available contains one light source, a blue light emitting diode (470 nm LED) and three detection channels. The amplification products are detected by means of fluorescent labeled hybridization probes which only emit fluorescence signals when they are bound to the target nucleic acid or in certain cases also by means of fluorescent dyes that bind to double-stranded DNA. A defined signal threshold is determined for all reactions to be analysed and the number of cycles Cp required to reach this threshold value is determined for the target nucleic acid as well as for the reference nucleic acids such as the standard or housekeeping gene. The absolute or relative copy numbers of the target molecule can be determined on the basis of the Cp values obtained for the target nucleic acid and the reference nucleic acid.

The fluorescence emitted by a sample is separated by a set of dichroic mirrors and filters into different wavelengths that can be recorded in one of the three detection channels (530/640/710 nm). This allows detection of the double-stranded DNA-binding dye SybrGreenI, mono color detection of the TaqMan Probe format and dual color detection of the Hybridization Probe (HybProbe) format. Details of the Lightcycler system are disclosed in WO 97/46707, WO 97/46712 and WO 98/46714, The complete contents of these applications are herewith incorporated by reference.

A very important feature of the LightCycler instrument is the color compensation software. In principle this software allows for accurate quantification and melting curve analysis by means of correcting spectral overlap of monitored fluorescent radiation in a temperature dependent manner. Technical details are disclosed in U.S. Pat. No. 6,197,520.

Similar to the LightCycler system, the Corbett Rotor-Gene Real time PCR Thermocycler (www.corbettresearch.com) is a 4 channel multiplexing system comprising 4 different LEDs as excitation sources and corresponding photodiodes as fluorescent detection units. Thus, although this instrument hardware at least theoretically has the capacity of performing multiplex experiments with up to four differently labeled hybridization probes within one reaction vessel, no respective successful application protocol has been published so far.

Another real time PCR instrument is the Biorad iQ Multicolor Real time PCR detection system (Cat. No: 170-8740), which allows for a fluorophore excitation and emission from 400 nm to 700 nm. The system is based on a conventional multiwell heating block for thermocycling, a tungsten lamp as an excitation source, a filter wheel for providing appropriate excitation wavelengths, a second filter wheel for selecting appropriate emission wavelengths and a CCD camera as a detection unit. The instrument has successfully been used in a multiplex assay for the detection of 4 different amplicons generated from targets with more or less equimolar concentrations, using four differently labeled TaqMan probes in the same reaction vessel (Pedersen, S., Bioradiations 107 (2001) 10-11).

In a further approach to increase multiplexing capacities, U.S. Pat. No. 6,369,893 discloses a real time PCR thermocycling instrument comprising a first optics assembly with at least two light sources and a second optics assembly comprising at least two detectors for detecting and discriminating light of different emission wavelengths. In particular, a specific embodiment of different 4 LEDs as light sources and 4 different photodiodes as detectors is disclosed. Thus, the instrument disclosed in U.S. Pat. No. 6,369,893 in principle can be used for real time PCR detection with a broad selection of different fluorescent dyes which are known in the art. Yet, U.S. Pat. No. 6,369,893 does neither anticipate nor suggest any approach on how a multiplex experiment comprising multiple different probes each labeled with a different fluorescent entity needs to be designed.

Real Time PCR Detection Formates

In general, there exist different formates for real time detection of amplified DNA, of which the following are well known and commonly used in the art:

a) DNA Binding Dye Formate

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SybrGreenI, for example, do not affect the efficiency of the PCR reaction.

All other formates known in the art require the design of a fluorescent labeled Hybridization Probe which only emits fluorescence upon binding to its target nucleic acid.

b) TaqMan Probe

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. No. 5,538,848).

c) Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

d) Single Label Probe (SLP) Format

This detection format consists of a single oligonucleotide labeled with a single fluorescent dye at either the 5'- or 3'-end (WO 02/14555). Two different designs can be used for oligo labeling: G-Quenching Probes and Nitroindole-Dequenching probes.

In the G-Quenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe.

In the Nitroindole Dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

e) FRET Hybridization Probes

The FRET Hybridization Probe test format is especially useful for all kinds of homogenous hybridization assays (Matthews, J. A., and Kricka, L. J., Analytical Biochemistry 169 (1988) 1-25. It is characterized by a pair of two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound, which is typically 10-100 Angstroem.

Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probeformat has been proven to be highly sensitive, exact and reliable (WO 97/46707; WO 97/46712; WO 97/46714). Yet, the design of appropriate FRET Hybridization Probe sequences may sometimes be limited by the special characteristics of the target nucleic acid sequence to be detected.

As an alternative to the usage of two FRET hybridization probes, it is also possible to use a fluorescent-labeled primer and only one labeled oligonucleotide probe (Bernard, P. S., et al., Analytical Biochemistry 255 (1998) 101-107). In this regard, it may be chosen arbitrarily, whether the primer is labeled with the FRET donor or the FRET acceptor compound.

Besides PCR and real time PCR, FRET hybridization probes are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

There exist many different pairs of fluorescent dyes known in the art which according to the invention are principally capable of acting together as a FRET donor/FRET acceptor pair. Yet, prior to the present invention, no functional example has been disclosed, characterized in that 4 different FRET pairs have succesfully been used in a multiplex detection assay. Among other reasons, this may be due to lack of appropriate instrumentation and, moreover, due to fact that the functionality of the FRET process of a specific FRET pair is interfered by other fluorecent compounds which are present in the same reaction mixture.

As discussed above, there exist different real time detection thermocycler instruments having a maximum of 4 detector channels for multiplex/multicolor detection. Yet, the utility of all of these instruments for multiplex detection up to now has been very limited due to the fact that attempts to establish real time multicolor multiplex assays with several (at least more than two) differently labeled probes with sufficient sensitivity and specificity have not been successful so far.

Thus, it was the object of the present invention to provide an improved system which allows for an optimized and at the same time flexible design of multiplex/multicolor detection experiments. In one aspect the problem to be solved relates to improvements in the design of approriate hybridization probes. In another aspect, the problem to be solved relates to an improvement of instrumentation.

BRIEF DESCRIPTION OF THE INVENTION

Thus, the new invention is directed to a real time PCR system with an extension of applicable detection formats and multicolor features. The system comprises specific reagent mixtures for multiplex/multicolor detection as well as an improved real time PCR instrument with an optical detection system comprising multiple detection units. The optical system is designed to provide excitation sources and detection channels for multiple detection formats, for example: SybrGreenI, multiplex FRET-Hybridization Probes, and multiplex TaqMan probes.

More precisely, the invention is directed to a system for performing multi-color real time PCR, comprising a real time PCR instrument and a specific composition or reaction mixture for performing multiplex PCR:

The composition or reaction mixture of the present invention comprises at least 3, preferably 4-5 and most preferably exactly 4 pairs of FRET hybridization probes. Each pair of said hybridization probes consists of a FRET donor probe carrying a FRET donor moiety and a FRET acceptor probe carrying a FRET acceptor moiety having an emission maximum between 550 and 710 nm.

In one embodiment at least 3, preferably at least 4 and most preferably exactly 4 FRET donor moieties are identical. Most preferably, all FRET donor moieties are identical. In other words, if all FRET donor moieties of the different FRET pairs are identical, they can be excited with the same excitation source.

In another embodiment of the invention at least 3, preferably at least 4 and most preferably exactly 4 FRET donor moieties are Fluorescein. Most preferably, all FRET donor moieties are Fluorescein.

In a specific embodiment, at least one additional FRET donor moiety is selected from a group consisiting of Atto425 and WI343.

In another specific embodiment, which is not at all mutual exclusive to those embodiments disclosed above, one FRET acceptor moiety is selected from a group consisting of LC-Red 705, Cy5.5, JA286 and a sulfonated cyanine dye as disclosed in U.S. Pat. No. 6,027,709, formula 1.

As a second FRET acceptor moiety Cy5 may be selected.

As a third FRET acceptor moiety, LC-Red 640 may be used.

As a fourth FRET acceptor moiety, the LCRed derivative LC-Red 610 is chosen.

In a particular embodiment, the fifth FRET acceptor moiety is selected from a group consisting of Rh6G and TAMRA.

The instrument part of the system is characterized in that said real time PCR instrument comprises
   at least 1 light source, preferably an LED
   at least 4 and preferably 5-6 fluorescent detector entities, each of said entities having central detection wavelengths which are distinct from each other by at least 25 and preferably at least 30 nm
   characterized in that said detector entities are capable of
      simultaneously detecting maximum fluorescene emission of at least 3, preferably 4 and most preferably 5 differently labeled FRET Hybridization Probe pairs,
      simultaneously detecting maximum fluorescence emission of at least 2 differently labeled TaqMan hybridization probes, and
      detecting maximum fluorescence emission of SybrGreenI
   means for heating and cooling
   multiple reaction vessels for containing a reaction mixture.

In a prefered embodiment of the invention the instrument part of the system is characterized in that said real time PCR instrument comprises exactly one light source.

In this context it is understood that although the instrument is being capable of detecting fluorescence emission of the FRET format, the TaqMan format and the SybrGreen format, the term "simultaneously" means that within the same thermcycling protocol (i.e. within one run of the instrument), either at least 3 differently labeled FRET Hybridization Probes or at least 2 differently TaqMan probes or SybrGreenI are detected.

Preferably, the instrument comprises at least 24, more preferably 32 and most preferably 48 of said reaction vessels.

Also preferably, said centrally detected wavelengths are selected from a group of range of wavelengths, said group consisting of 520-540 nm, 545-565 nm, 570-590 nm, 600-620 nm, 630-650 nm, 660-680 nm, and 700-720 nm.

Also preferably, each reaction vessel is characterized in that fluorescence excitation by said fluorescent light sources and fluorescence monitoring by said fluorescent detector entities are obtained along the same axis of said reaction vessel.

It has been proven to be particular advantageous, if said light sources and said detector entities are located in separate housings.

It has also been proven to be particular advantageous, if said means for heating and cooling are means of forced liquid or forced gas, preferentially means of forced air.

It has further been proven to be particular advantageous, if the reaction vessels are fixed in a rotating carousel.

In a last aspect, the invention is also directed to a corresponding method for amplyfying and detecting multiple target DNA sequences comprising
   a) providing a reaction mixture as disclosed above,
   b) subjecting said reaction mixture to a thermoclyling protiocol such that amplification of said multiple target sequences can take place c) monitoring hybridization of each of said pairs of FRET hybridization probes at least once after a plurality of amplification cycles.

Hybridization may also be monitored at least once in a temperature dependent manner in order to perform a melting curve analysis.

DETAILED DESCRIPTION OF THE INVENTION

A) Instrument

In a first aspect, a system according to the invention comprises an instrument suitable for real time PCR. Optionally, the instrument is also suited for melting curve analysis, i.e. monitoring temperature dependent binding of a DNA binding entity such as a hybridization probe or a ds DNA binding dye.

The instrument basically consists of an optical part and a means for thermocycling which can subject multiple amplification solutions in their respective reaction vessels to a process of repeated thermocycling such that a polymerase chain reaction (PCR) can take place.

Preferably, the instrument part of the system is characterized in that said real time PCR instrument comprises
 at least 1 light source, preferably a light emitting diode
 at least 4 and preferably 5-6 fluorescent detector entities, each of said entities having central detection wavelengths which are distinct from each other by at least 25 and preferably at least 30 nm
  characterized in that said detector entities are capable of
   simultaneously detecting maximum fluorescene emission of at least 3, preferably 4 and most preferably 5 differently labeled FRET Hybridization Probe pairs,
   simultaneously detecting maximum fluorescence emission of at least 2 differently labeled TaqMan hybridization probes, and
   detecting maximum fluorescence emission of SybrGreenI
 means for heating and cooling, and
 multiple reaction vessels for containing a reaction mixture.

Most preferably, the instrument part of the system is characterized in that said real time PCR instrument comprises exactly one light source.

The means for thermocycling can be chosen arbitrarily. For example, metal block cyclers which are well known in the art may be used. Yet it is advantageous if the means for thermocycling provide means for active heating as well as independent means for active cooling. Moreover it has also been proven to be particular advantageous, if said means for heating and cooling are means of forced liquid or forced gas. In a specific embodiments said means use forced air.

It is also prefered, if said means for thermocycling are capable of performing rapid thermocycling like it is the case in the LightCycler technology (WO 97/46712). As it can be deduced from WO 97/46712, this technology is based on a forced air heating characterized in that ambient air is heated by a heating coil and forced air cooling characterized in that ambient air is provided.

A further improvement with respect to rapid thermocycling is the usage of capillaries as reaction vessels due to there comparatively high surface/volume ratio. Capillaries with an outer diameter of less than 5 mm, preferably of less than 3.2 mm and most preferably of less than 1,6 mm have been proven by the inventors to be particular advantageous, since they allow for reaction mixtures having total volumes between 10 and 100 µl which still can be subjected to a rapid thermocycling protocol with a reaction time of less than 2 minutes per cycle. Moreover, each reaction vessel needs to be fabricated at least partially or completely of an optically clear material such as glas or plastic.

Positioning of each reaction vessel (capillary) in a monitoring position is preferably characterized in that fluorescence excitation and monitoring are performed along the same axis of said reaction vessel. Such a principle enhances signalling due the phemomenon of total internal reflectance.

It has further been proven to be particular advantageous, if the reaction vessels are fixed in a rotating carousel in order to generate uniform thermocycling profiles throughout the multiple reaction vessels.

The optical part of the instrument basically consists of an excitation unit with one or more appropriate light sources in order to excite the fluorescent compound(s) which are present in the reaction solutions and a detection unit for detecting fluorescence emission from said reaction vessels.

According to WO 97/46712, it is possible to construct an optical system wherein the excitation unit and the detection unit are placed in a common housing, provided that an appropriate number of dichroidic mirrors is used. Yet, in the context of the present invention, it turned out to be advantageous, if the excitiation unit comprising the light sources and the detection unit comprising the detector entities are located in separate housings with the result that the improved real time PCR instrument comprises two separate optical units.

For the excitation unit, either monochromatic excitation or polychromatic excitation may be used according to the invention. For monochromatic excitation, either a monochromatic LED (light emitting diode) or a monochromatic laser may be used. It is also possible to use instruments with two or multiple LEDs or monochromatic lasers but only using one at a time in an individual measurement. For polychromatic excitation, a white LED, a Halogen lamp or a Xenon lamp may be used. In this case either a filter wheel or other means for moving appropriate filters into and out of the excitation beam need to be installed in the instrument such that light with different selective excitation wavelengths can be provided.

The optical features of the excitation unit according to the invention are selected according to different parameters that have to be considered:

First, the shortest excitation wavelength should be longer than 360 nm and preferably longer than 400 nm, since short wavelength radiation has compartively low transmission rates through conventionally used optical material which is used for real time PCR reaction vessels such as glas or plastic. In addition, excitation with higher wavelengths for example in the range of 400-500 nm avoids interference of intrinsic fluorescence from the material of the reaction vessels which might disturb monitoring of the reaction.

In a prefered embodiment of the invention, the excitation unit consists of only one light source, because according to the present invention even with a single light source it is possible to perform a multiplex detection in real time PCR. Moreover, a multiplex detection in real time PCR is even possible with a single, monochromatic light source.

In one embodiment, the excitation unit comprises a blue LED emitting at 470 nm. FIG. 1 shows the excitation spectra for different fluorescent dyes which may be used according to the present invention. Among these dyes, Fluorescein as a frequently used FRET donor compound or TaqMan reporter dye known by a person skilled in the art can be excited with a single light emitting diode having an excitation wavelength of 470 nm, whereas frequently used FRET acceptor dyes are only excited marginally with 470 nm LED.

In addition, a second UV-LED emitting in between 400 and 430 nm, preferably at 415 nm may be used optionally for exciting other FRET donor compounds having a shorter excitation maximum as compared to Fluorescein.

More precisely, the blue 470 nm LED is capable of exciting Fluorescein, which is used in the HybProbe format as donor dye in combination with 4 different acceptor (reporter) dyes. On the other hand, typical FRET acceptor dyes such as LC-Red-640 or Cy5 are only excited marginally by the 470 nm LED. The blue LED may also excite the reporter dyes FAM and HEX or VIC in dual color TaqMan assays. In addition, Fluorescein is used as reporter dye in the Single Label Probe (SLP) format. Moreover, the blue LED is used to excite SybrGreenI for non probe based detection of amplification products.

The optional UV LED may be used in the HybProbe format to excite a short wavelenth donor dye in combination with approriate reporter dyes that emit fluorescence at comparatively short wavelengths. Moreover, a third LED emitting at 580 nm may be included.

For the detection unit, different modes of detection which are known in the art can be used according to the invention. For example, it is well known in the art to use several photodiodes characterized in that each photodiode is capable of detecting fluorescent light of a specific wavelength. In one aspect of the invention, a detection system having exactly five or six channels using photodiodes as detectors is provided. As it will be shown, such embodiments already enable for a simultaneous 4 color FRET Hybridization Probe detection.

The optical features of the detection unit according to the invention are selected according to the following different parameters:

First of all, the longest emission wavelength that should be detected is around less than 800 nm, and preferably less than 730 nm, since detection of higher wavelength signals is affected by a possible background of putative infrared radiation by the heating part of the instrument. Moreover, long wavelength infrared dyes which are known in the art have a suboptimal quantum yield, are less stable and thus more difficult to couple to a desired hybridization probe.

As a result, the different detection channels should have central detection maximae between 500 and 800 nm and preferably between 520 and 730 nm. In this context, FIG. 2 shows the emission spectra for different fluorescent dyes which may be used according to the present invention.

Within the range of 500 and 800 nm, the detection channnels can be defined exactly by means of seleting appropriate filters which the light beam has to pass prior to entering the respective photodiode. For appropriate selection, the following parameters have been identified by the inventors to be considered:

First, the central wavelength detection maximum of each channel should be chosen dependent on the maxima of the emission spectra of those fluorescent dyes that shall be detected predominantly. As a rule of thumb, for appropriate detection sensitivity, the maximum of the fluorescent emission from the dye to be detected should not differ more than +/−10 nm from the centrally detected wavelength of each channel.

Moreover, all detection channels should be able to detect discrete emissions, i.e. the spectral overlap should be minimized as far as possible. In this regard, it is advantageous, if the half band widths of each channel is 40 nm or less. More advantageously, the half band widths of each channel is 20 nm or less.

Preferably, crosstalk of the fluorophores to be detected in neighboring channnnels is less than 70%, more preferably less than 50% und most prefered less than 30%. Another important criterium in this regard is the blocking value, which is indicative for the maximum intensity that is detected outside the specified transmission range of the channel (filter). Preferably, this value is less than $10^{-3}$.

Based on these criteria, it has been proven to be advantageous, if the centrally detected wavelenghts of each of the 5-6 channels according to the invention are separated from each other by more than 25 nm and preferably even more than 30 nm.

In one embodiment, said centrally detected wavelengths are selected from a group of range of wavelengths, said group consisiting of 520-540 nm, 545-565 nm, 570-590 nm, 600-620 nm, 630-650 nm, 660-680 nm, and 700-720 nm.

Moreover, in one specific embodiment consisting of 6 detector channels said channels having centrally detected wavelengths at around 530, 580, 610, 640, 670, and 710 nm+/−5 nm or 530, 555, 610, 640, 670, and 710 nm+/−5 nm or preferably +/−2 nm.

In another specific embodiment consisting of 5 detector channels said channels have centrally detected wavelengths at around 530, 610, 640, 670, and 710 nm+/−5 nm or preferably +/−2 nm.

In a third specific embodiment consisting of 4 detector channels said channels have centrally detected wavelenghts at around 610, 640, 670, and 710 nm+/−5 nm or preferably +/−2 nm.

As an example, FIG. 3 shows the 6 detection channels of a prefered embodiment and the emission spectra for different fluorescent dyes which may be used according to the present invention. In this embodiment, the six channels are separated by at least 25 nm spectral distance to minimize the crosstalk from each reporter dye into neighboring detection channels. The detection unit is capable of detecting SybrGreenI and the TaqMan reporter dye Fluorescein/FAM in the channel having its central wavelength detection maximum around 530 nm. In addition, the system is preferentially capable of detecting HEX/VIC in a second channel around 560 nm. Further long wavelength detection channels are capable of detecting HybProbe acceptor dyes and optionally long wavelength SLP reporter dyes.

The excitation and detection unit are connected by a multiple-leg fiber bundle. Emitted light from the reaction vessels (e.g. the glas capillaries) is homogeneously distributed using a lightpipe and is transmitted into six glas fiber bundles. These bundles of 50 μm single glas fibers transmit the light into each of the six detection channels.

This set up of excition unit and detection unit located in separate housings provides two advantages compared to the optical unit as disclosed in WO 97/46712: Homogeneous distribution of emitted light into all six detection channels and mechanical decoupling of the excitation and detection unit. This enables highly precise positioning of the excitation unit towards the reaction vessels to become monitored (e.g. capillary tips) without moving the detection unit. Moreover, the number of necessary dichrodic mirrors is minimized. An example of such a set up is shown in FIG. 4, which discloses a possible embodiment of the invention. As it can be seen, excitation and detection unit are located in different housings.

In addition, the system according to the invention comprises a color compensation tool as disclosed in detail in U.S. Pat. No. 6,197,520 which is incorporated into this application in its entirety by reference. The corresponding software enables for measuring fluorescence throughout a range of temperatures and correcting for temperature dependent spectral overlap of the 6 detector channels disclosed above.

In principle this is achieved by
a) providing calibrator solutions for each fluorescent entity which is incorporated in the multiplex experiment to become performed
b) monitoring temperature dependent fluorescene of each of said solutions in each of the detector channels in order to determine the temperature dependent amount of crosstalk between different channels, and
c) generating a color compensation data set containing correction values.

B) Test Formats and Selection of Dyes

In the context of the present invention, the term "multiplex PCR" is understood as a PCR reaction characterized in that 2 or more different amplification products are generated by means of using 2 or more pairs of amplication primers in the same PCR reaction.

Also in the context of the present invention, the term "multicolor real time PCR" is defined as an real time PCR assay characterized in that 1 or more different amplification products generated either in a multiplex PCR or in a monoplex PCR (using only 1 pair of amplification primers) are detected by differently labeled hybridization probes.

A major aspect of the present invention is based on usage of differently labeled hybridization reagents, each reagent comprising a pair of FRET hybridization probes comprising a pair of two fluorescent dyes which interact with each other on the principle of fluorescence resonance energy transfer (FRET). According to the invention, appropriate dye pairs can be selected for the labeling of a hybridization reagent which may be used for detection in at least three or four and preferably as much detection channels as possible.

More precisely, such a hybridization reagent is composed of two adjacently hybridizing oligonucleotides, appropriately labelled such that together they can act according to the FRET-HybProbe detection format as disclosed in WO 97/46707, WO 97/46712, and WO 97/46714). In many cases, it is sufficient if the hybridization reagent consists of a single oligonucleotide or in case of the FRET hybprobe format, of a pair of oligonucleotides acting together as a donor probe and an acceptor probe. Yet, in other cases there may exist many other sequence variants in the target sequences which need to be detected. Thus it may be impossible to detect the sequences of all members by just using just one pair of FRET oligonucleotide hybridization probes.

For those cases, a hybridization reagent may consist of 1, 2 or more hybridization probes, which are similar and bind to homologous sequences, but differ from each other by 1, 2, 3 or more mononucleotide-, dinucleotide- or trinucleotide exchanges, deletions or additions. In case of the hybridization reagent being a pair of FRET hybridization probes, said hybridization reagent may consist of 1, 2, 3, or more FRET donor oligonudeotide probes and/or 1, 2, 3, or more acceptor oligonudeotide probes. In this case all donor probes may be similar, but differ from each other by mononucleotide-, dinudeotide- or trinucleotide exchanges, deletions or additions. As well, all acceptor probes may be similar, differ from each other by mononucleotide-, dinudeotide- or trinucleotide exchanges, deletions or additions.

In addition it is also within the scope of the present invention, if multi-color FRET detection is performed wherein one member of said pair of labeled hybridization probes is replaced by an appropriately labeled primer as disclosed in Bernard, P. S., et al., Analytical Biochemistry 255 (1998) 101-107. Moreover, it is also within the scope of the present invention, if instead of an increase in fluorescenct emission from a respective FRET acceptor compound, the decrease in fluorescent emission of one, several, or all FRET donor moieties is monitored as being indicative for the presence of the target nucleic acid to be detected.

In addition to the various possibilites for performing multi-color detection based on the FRET principle, the system of the invention also allows for the performance of other detection formates such as detection of the target nucleic acid by means of SybrGreenI, multiplex detection using differentially labeled Molecular Beacons, Single Labeled Probes or dual color TaqMan detection. As it known in the art, dual color TaqMan assays may be based on the use of Cy 5 (Amersham) as Quencher compounds in combination with FAM as a first standard reporter dye and either HEX or alternatively VIC as a second reporter compound.

In principle, there exist multiple possibilities of fluorescent dye combinations, which together may act as a FRET pair (Review: Resonance Energy Transfer Editors: Meer, B Wieb van der et al., VCH Publishers INC., 1994). However, based on the instrumental preconditions it is not trivial for person skilled in the art to develop a multi-color test which combines multiple FRET hybridization reagents that do not interfere with each other in such a way that sensitivity and/or specificity of a respective real time PCR experiment are affected.

Regarding the selection of approriate pairs of FRET hybridization probes for example, the dyes used for FRET donors and FRET acceptors can not be chosen arnbitrarily but need to fulfill at least the following requirements:

sufficient solubility and capability of being coupled to an oligonkleotide
stability of the dyes under PCR thermocycling conditions
sufficient and reproducible emission intensity and quantum yield
low temperature dependence of emission intensity
essentially no spectral shifts under different chemical conditions
essentially no spectral shifts when coupled to different oligonucleotide sequences
discrete spectral emission maxima
availability of a suitable partner dye for performing a FRET process As a consequence, one important aspect of the system according to the invention is focussed on identification of multiple Fluorescence Resonance Energy Transfer (FRET) dye pairs usable in the HybProbe format for as many detection channels as possible. Excitation and emission spectra of dyes FRET dye pairs that enable a 4- or 5-plex multi-color detection set up are already shown in FIG. 1-3. Alternatives wil be be described below.

In this regard, the following table summarizes various FRET acceptor dyes and TaqMan reporter dyes which have succesfully been used so far in the indicated detection channels performing either a 4-color FRET Hybridization Probe assay or a dual color TaqMen asssay:

TABLE 1

| Channel | FRET Acceptor dye | TaqMan Reporter dye |
| --- | --- | --- |
| 530 (also detection of SybrGreenI) | — | Fluorescein (Fam) Coumarine |
| 555 | Rh6G Tamra | Hex Vic Tamra |
| 580 | | Tamra ROX |
| 610 | LCRed610 | TexasRed |

TABLE 1-continued

| Channel | FRET Acceptor dye | TaqMan Reporter dye |
| --- | --- | --- |
| 640 | LCRed640 | |
| 670 | Cy5 | |
| | Bodipi 655 | |
| | Alexa 647 | |
| 710 | Ja286 | |
| | Cy5.5 | |
| | LCRed705 | |

Yet, for several of the different reporter entities indicated above, different FRET donor moieties (Donor) and TaqMan quencher compounds (Q) respectively have to be used depending on the excitation wavelength which is available due to the presence of either one, two or three different LEDs. Therefore, different possibilities of appropriate FRET pairs or TaqMan combinations are summarized in the following more comprehensive table:

WI 343 is a derivative of Coumarin 343 (Aldrich, Cat. No. 55 804 654), which is coupled with a linker (beta alanin) and transformed to the succinimidyl ester according to standard methods:

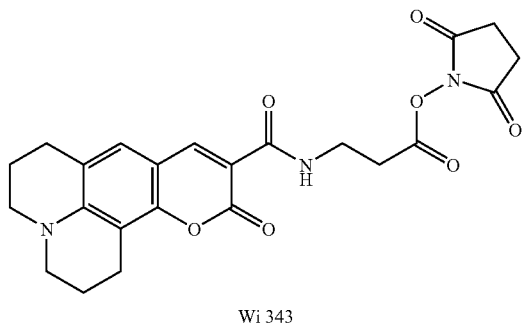

Wi 343

TABLE 2

| | LED | 530 | 555 | 580 | 610 | 640 | 670 | 710 |
| --- | --- | --- | --- | --- | --- | --- | --- | --- |
| FRET: | | | | | | | | |
| Donor: Atto 425 WI 343 | 410 | — | Rh6G TAMRA | — | LCRed 610 | LCRed 640 | Cy5 Bodipy655 Alexa647 | JA286 LCRed705 Cy5.5 |
| Donor: Fluorescein | 470 | — | — | — | LCRed 610 | LCRed 640 | Cy5 Bodipy655 Alexa647 | JA286 LCRed705 Cy5.5 |
| Donor: LCRed 640 | 590 | — | — | — | — | — | Cy5 Bodipy655 Alexa647 | JA286 LC705 Cy5.5 |
| TaqMan: | | | | | | | | |
| Q: Arbitrary | 410 | Coumarine | — | — | — | — | — | — |
| Q: Tamra | 470 | Fam | Hex Vic | — | — | — | — | — |
| Q: Cy5 | 470 | Fam | Hex Vic TAMRA | TAMRA Rox | — | — | — | — |
| Q: BHQ | 470 | Fam | Hex Vic TAMRA | TAMRA Rox | — | — | — | — |
| Q: Cy5 | 590 | — | — | — | Texas-Red | — | — | — |
| Q: BHQ | 590 | — | — | — | Texas-Red | — | — | — |

The dyes mentioned in the tables above are available as follows:

LC-Red-705 and LC Red-640 are available from Roche Applied Science (Cat. No. 2 015 161 and 2 157 594)

LC-Red 610 is synthesized according to standard protocols using a fluorescent dye as disclosed in U.S. Pat. No. 5,750,409, compound II JA 286 is disclosed in EP 0 747 447, example 1. For this dye, it is advantageous, if this dye is connected to the hybridizing oligonucleotide by a long non hybridizing spacer moiety of five nucleotide residues.

Cy-5 NHS-ester is available from Amersham, (Cat. No. PA 15100) and Cyc 5.5 Phosphoramidite is also available from Amersham (Cat. No 271799 01).

Bodipy 650/665 NHS-Ester and Alexa 647 NHS Ester are available from Molecular Probes (Cat. Nos D1 000 1 and A 2 000 6).

Atto 425-NHS ester is available from Attotec (Cat. No. AD 425-3).

In addition, all TaqMan dyes are available from different suppliers known by a person skilled in the art, for example Molecular probes.

The BlackHole Quencher (BHQ) is available from Biosearch Technologies (Cat. No. BHQ 1-3)

Appropriate labeling of oligonucleotide probes may be performed by conventional methods known by a person skilled in the art. In particular, labeling may be practiced using either fluorescent compounds that comprise an activated NHS-ester or fluorescent compounds linked to a Phosphoramidite, such that labeling can be performed during a de-novo oligonucleotide synthesis itself. Furthermore, a Fluorescein-labeled probe may be prepared by using a Fluorescein Controlled Pore Glass particle as a solid support (Roche Applied Science Cat. No. 3 138 178) for oligonucleotide synthesis.

C) Methods and Kits

In a further aspect, the invention is directed to methods of performing multiplex PCR by means of using all different embodiments of the systems, instruments and compositions disclosed above.

In particular, the present invention is directed to a method for amplifying and detecting multiple target DNA sequences comprising
  providing a composition or reaction mixture according to the invention,
  subjecting said reaction mixture to a thermocyling protocol such that amplification of said multiple target sequences can take place, and
  monitoring hybridization of each of said pairs of FRET hybridization probes at least once after a plurality of amplification cycles.

In a specific embodiment, hybridization is monitored at least once in a temperature dependent manner.

The composition or reaction mixture predominantly comprises at least 3, preferably 4-5, and most preferably exactly 4 pairs of FRET hybridization probes, each pair of hybridization probes consisting of a FRET donor probe carrying a FRET donor moiety and a FRET acceptor probe carrying a FRET acceptor moiety having an emission maximum between 550 and 710 nm.

In addition, such a composition or reaction mixture according to the invention may comprise one or several or preferably all compounds and reagents selected from the following list:
  Buffer, applicable for a polymerase chain reaction
  Deoxynucleoside triphosphates
    Template dependent DNA polymerase, preferably thermostable,
    at least one pair or several pairs of amplification primers In yet another aspect, the invention is directed to a kit comprising at least a first set of amplification primers and at least three, four, or five pairs of FRET hybridization probes.

In addition, such a kit according to the invention may comprise one or several other compounds and reagents selected from the following list:
  Buffer, applicable for a polymerase chain reaction
  Deoxynucleoside triphosphates
  Template dependent DNA polymerase, preferably thermostable,
  At least one or multiple pairs of amplification primers Such a kit may also comprise an internal control DNA, which can be amplified and detected using the same primers and probes as used for the detection of any target nucleic acid. Each of the components disclosed above may be stored in a single storage vessel. Yet, any combination of components for storage within the same vessel is possible as well.

D) BEST MODE OF THE INVENTION

The best mode of the invention known by the inventors at the date of filing the application is as follows:

In this prefered embodiment, a system according to the invention provides a photometer with one or two excitation sources and six detection channels. A blue (470 nm) and optionally an UV (410 nm) light-emitting diode are combined with detection channels having central detection wavelengths at 530, 555, 610, 640, 670 and 710 nm.

The photometer of the improved real time PCR instrument comprises two separate optical units. As disclosed in FIG. 4, excitation and detection unit are located in different housings.

(I) An excitation unit with one or two LED's: A blue LED emitting at 470 nm and optionally a violet LED emitting at 415 nm. The blue LED is capable of exciting SybrGreenI and Fluorescein. Fluorescein is used in the HybProbe format as donor dye in combination with 4 different acceptor (reporter) dyes: Red 610, Red 640, Cy 5, Red 705. Furthermore the blue LED excites the reporter dyes FAM and HEX or VIC in dual color TaqMan assays. In addition, fluorescein is used as reporter dye in the Single Label Probe (SLP) format. The optional violet LED may used in the HybProbe format to excite a short wavelenth donor dye (Atto 425)) in combination with a reporter dye at 555 nm (Rh6G).

(II) A detection unit with six channels using photodiodes as detectors. The six channels are separated by at least 25 nm spectral distance to minimize the crosstalk from each reporter dye into neighboring detection channels. The detection unit is capable of detecting SybrGreenI and fluorescein/FAM in the 530 nm channel. In addition, the system is capable of detecting HEX/VIC and RH6G a in the 555 nm channel. The long wavelegth detection channels (610, 640, 670, 710 nm) are capable of detecting HybProbe acceptor dyes and optionally for long wavelength SLP reporter dyes.

The excitation and detection unit are connected by a six-leg fiber bundle. Emitted light from the glas capillaries is homogeneously distributed using a lightpipe and is transmitted into six glas fiber bundles. These bundles of 50 μm single glas fibers transmit the light into each of the six detection channels. This setup provides two advantages compared to the LC 1.2 optical unit: Homogeneous distribution of emitted light into all six detection channels and mechanical decoupling of the excitation and detection unit. This enables highly precise positioning of the excitation unit towards the capillary tips without moving the detection unit. An effective color compensation function allows simultaneous detection of multiple targets in different channels.

Combined with these hardware and software features, multicolor capabilities of the system in order to perform Multiplex FRET Hybridization Probedetection have been established. In addition, the system of according to the invention allows for other non FRET-Hybprobe detection formats.

Based on the Hybridization Probe detection format, the system enables at least 4-color multiplexing of real-time quantification and melting curve analysis. Taking a melting curve resolution of six melting peaks per channel into consideration, up to 24 different PCR products are discernable using the photometer according to the invention. To enable this, new previously unknown FRET-acceptor dyes have been developed for detection channels with central emission wavelengths at 610 and 670 nm. In addition, the optional 410 nm LED provides an option for using a short wavelength donor dye in combination with an acceptor dye emitting at 555 nm thus providing a fifth HybProbe detection channel. Excitation and emission spectra of specifically useful dyes are shown in FIGS. 1 and 2.

Using fluorescein as FRET donor dye two new FRET acceptor dyes could be identified being detectable in the 610 nm channel (Red 610) and in the 670 nm channel (Cy 5) respectively. Both dyes show high signal dynamics when used in the HybProbe FRET format. In addition, the spectral properties of the dyes fit perfectly into the photometer disclosed above thus minimizing the crosstalk into heterologous detection channels. Using a flexible multiple-channel color compensation algorithm it is shown that specific detection of all 4 FRET acceptor dyes (including the already existing dyes LC Red 640 and LC Red 705) from a single reaction is feasible over a temperature range from 40° C. to 95° C.

When trying to identify a fifth FRET acceptor dye for the 555 nm channel it turned out that good FRET signal dynamics is inhibited by two effects:

(I) The fluorescein donor dye shows a high crosstalk into the 555 nm channel thus masking increasing signals of a potential FRET acceptor dye during the PCR process.

(II) A FRET acceptor dye emitting at 555 nm is itself directly excited by the 470 nm LED thus increasing the background fluorescence significantly and consequently lowering the detection sensitivity.

A solution to these drawbacks was found by using a 410 nm UV LED for excitation of a short wavelength donor dye (Atto 425) in combination with a suitable 555 nm acceptor dye (Rh6G). In this combination, crosstalk from the donor into the 555 nm detection channel and direct excitation of the FRET acceptor were minimized and sufficient signal dynamics was achieved after color compensation.

Furthermore, it turned out that the short wavelength donor Atto 425 can even be used in combination with all long wavelength acceptor dyes. Unexpectedly, FRET signal dynamics of long wavelength acceptors in combination with Atto 425 are comparable to signal dynamics when used in combination with fluorescein. This observation provides an option to extend multi color features to a 5-channel format using just one donor dye.

Using the TaqMan detection format, dual color applications based on standard TaqMan reporter dyes FAM (detected at 530 nm) and HEX or VIC (detected at 560 nm) can be performed without major modifications of the TaqMan chemistry known in the art. The obtained detection sensitivity is comparable to the COBAS TaqMan instrument (Roche Molecular Systems).

Furthermore, the Single Labeled Probes (SLP's) format for melting curve analysis (WO 02/14555) is applicable within a system according to the invention. This format is based on quenching or, respectively, de-quenching of the probe-label after hybridization to its target sequence. The format requires just one probe terminally labeled with a single dye. Compared to HybProbe or TaqMan formats, SLP's thus enable a significantly less expensive setup of assays for integrated analysis of Single Nucleotide Polymorphisms (SNP's). By reporting melting temperatures, different alleles of an SLP can unambiguously be distiguished in a single reaction. Multiplexing options are provided by using different reporter dyes.

Possibilities for Real time multicolor PCR detection in the above disclosed instrument are summarized in the following table:

TABLE 3

| Assay Format | Detection Channels (Reporter Dyes) |
|---|---|
| SYBR Green I | 530 nm (SYBR Green I) |
| HybProbes | 610 nm (LC RED 610) |
|  | 640 nm (LC RED 640) |
|  | 670 nm (LC RED 670) |
|  | 710 nm (LC RED 705) |
| Hydrolysis Probes (TaqMan Probes) | 530 nm (FAM) 555 nm (VIC, HEX) |
| SimpleProbes | 530 nm (Fluorescein) |

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Quantitative real time PCR of Factor V DNA using different pairs of FRET hybridization probes labeled with different fluorescent compounds For amplification of a Factor V DNA fragment, 4 different 100 μl real time PCR reaction mixtures were set up as follows:
$10^6$ copies of a plasmid containing Factor V gene

| | | |
|---|---|---|
| 3 | mM | $MgCl_2$ |
| 500 | nM each | primers |
| 200 | nM | FRET 3'Hybridization Probe according to Seq. A |
| 200 | nM | FRET 5'Hybridization Probe according to Seq. B1, B2, B3 or B4, respectively. |

In addition, PCR components from the LightCycler DNA Hyb Probes Kit (Roche Applied Science, Cat. No. 2158825) were used.

Primers and probes were used as follows:
Primer FactorV, forward:

5'-GAG AGA CAT CGC CTC TGG GCT A-3' (22-mer) (Seq. ID. No: 1)

Primer FactorV, reverse:

5'-TGT TAT CAC ACT GGT GCT AA-3' (20-mer) (Seq. ID. No: 2)

A: 3'Fluorescein labeled Hybridization Probe

5'-AAT ACC TGT ATT CCT CGC CTG TC-3' (23-mer) (SEq. Id. No: 3)

B1: 5' Red610 Hybridization Probe

```
5'-AGG GAT CTG CTC TTA CAG ATT AGA AGT AGT CCT ATT-3'   (36-mer)
```

B2: 5' Red640 Hybridization Probe

```
5'-AGG GAT CTG CTC TTA CAG ATT AGA AGT AGT CCT ATT-3'   (36-mer)
```

B3: 5' Cy5 Hybridization Probe

```
5'-AGG GAT CTG CTC TTA CAG ATT AGA AGT AGT CCT ATT-3'   (36-mer)
```

B4: 5' Red705 Hybridization Probe

```
5'-AGG GAT CTG CTC TTA CAG ATT AGA AGT AGT CCT ATT-3'   (36-mer)
```

(B1-B4: Seq. Id. NO: 4)

Amplification was performed in a LightCycler instrument disclosed above as best mode of the invention according to the following thermocycling protocol:

| | T[° C.] | t[sec] | Ramp-rate [° C./sec] | Acquisition | Cycles |
|---|---|---|---|---|---|
| Denaturation | 95 | 30 | 20.0 | none | 1 |
| Amplification | 95 | 10 | 20.0 | none | |
| | 55 | 20 | 20.0 | single | 45 |
| | 72 | 20 | 20.0 | none | |

Real time monitoring was performed with and without a color compensation algorithm and using the $2^{nd}$ derivative threshold method over 45 cycles by measuring the fluorescence signals in a detection channel and using arithmetic background correction for normalization of initial fluorescence background intensities.

Results are shown in FIG. 5a-5d. As can be seen in the figures, specific and quantitative amplification signals of all used FRET acceptor dyes could be obtained after color compensation in the corresponding 610, 640, 670 and 710 nm detection channels. Moreover, it is shown that the spectral overlap of the different dyes in the neighboring channels did not affect specific and quantitatve signalling when appropriate color compensation is performed.

EXAMPLE 2

4-Color Melting Curve Analysis

Figure 1:
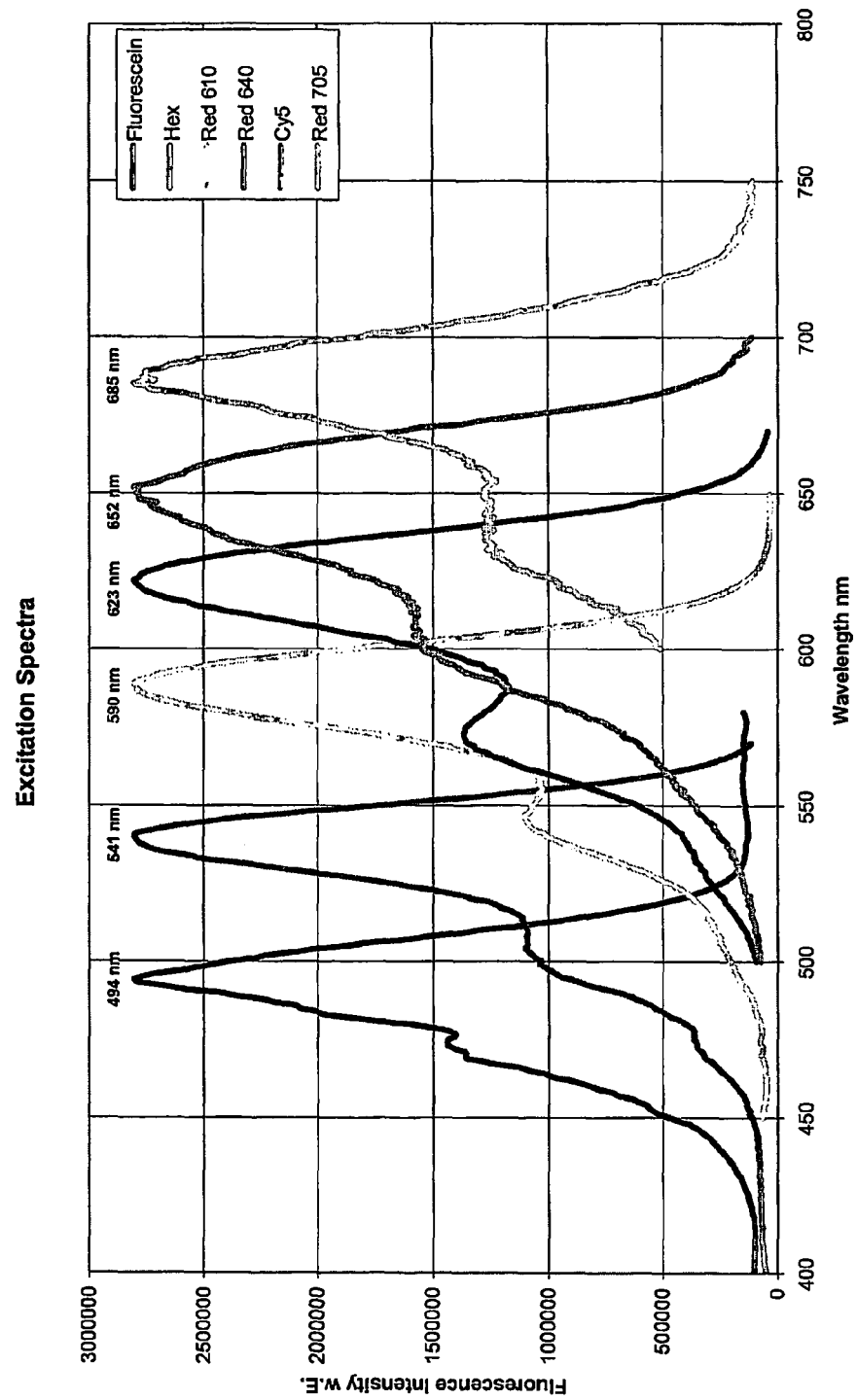
FIG. 1 Excitation spectra of FRET donor and acceptor dyes for the present invention
FIG. 2 Emission spectra of FRET donor and acceptor dyes for the present invention
FIG. 3 Emission spectra of FRET donor and acceptor dyes and detection channels for the present invention
FIG. 4 Photometer setup
FIG. 5 4 color real time PCR quantification experiment of example 1
FIG. 6 Primer/probe design of example 2
FIG. 7 4-color Real time PCR melting curve experiment of example 2
FIG. 8 Dual color TaqMan Real time PCR quantification experiment of example 3
Figure 2:
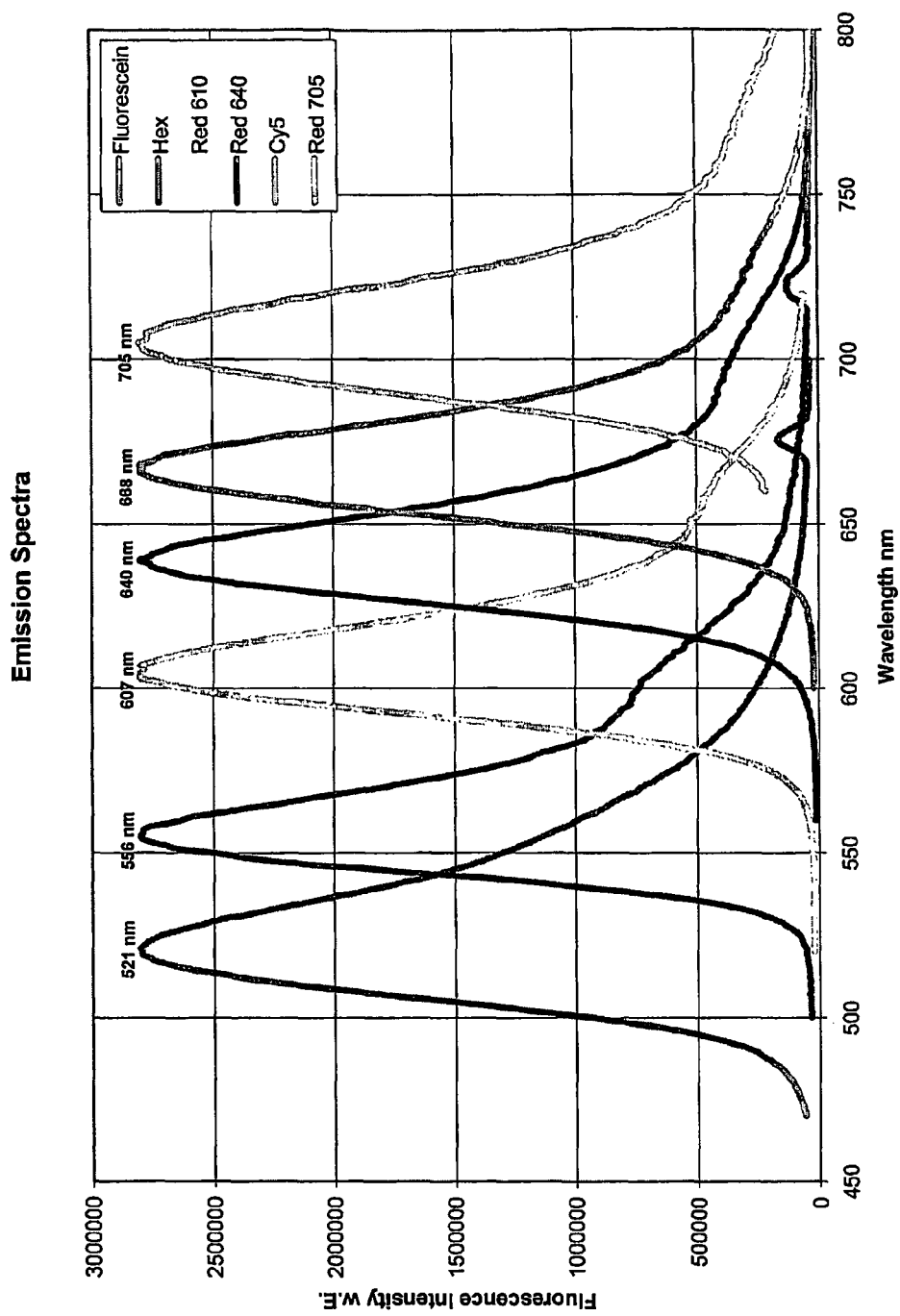
Figure 3:
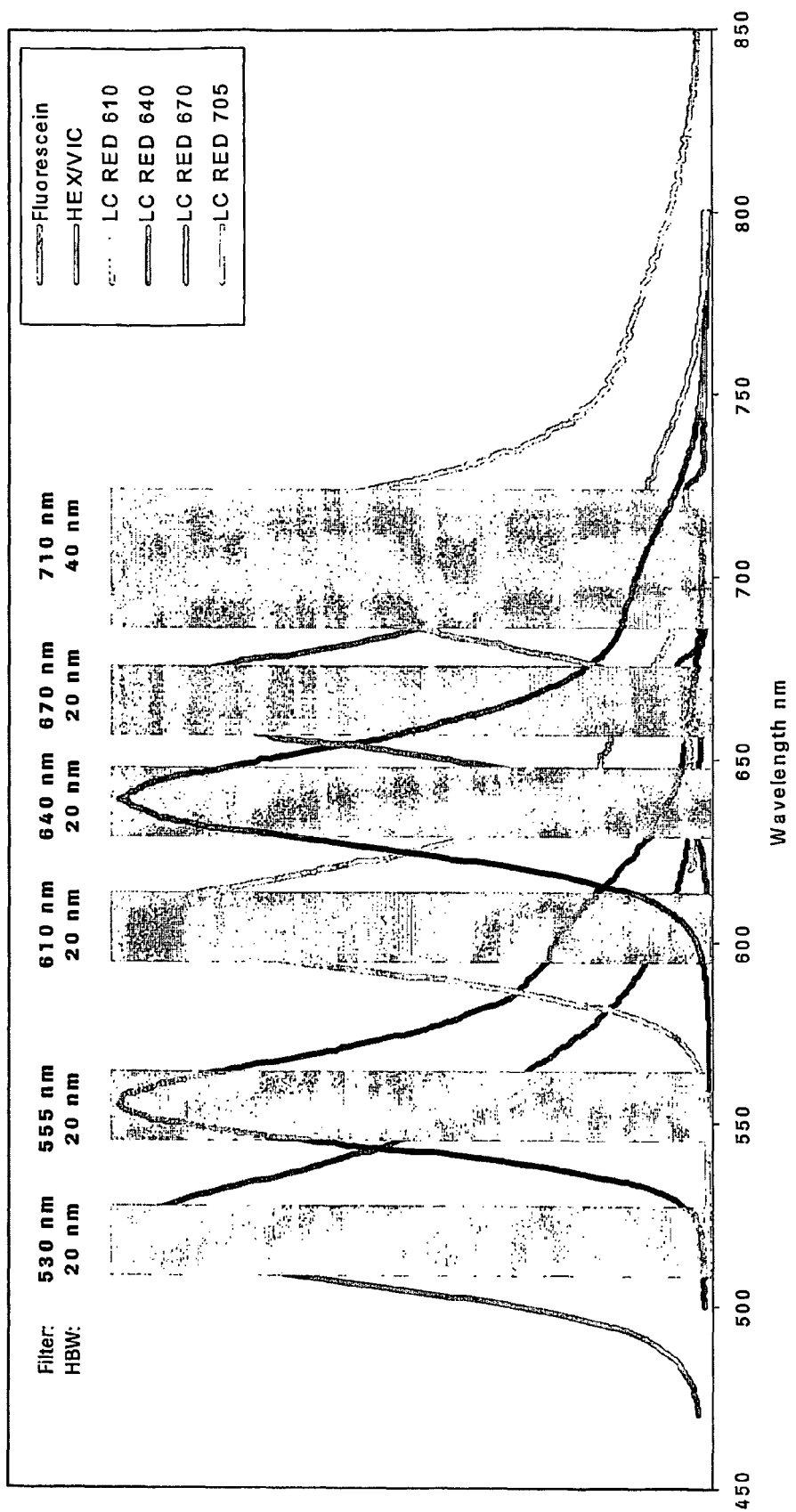
Figure 4:
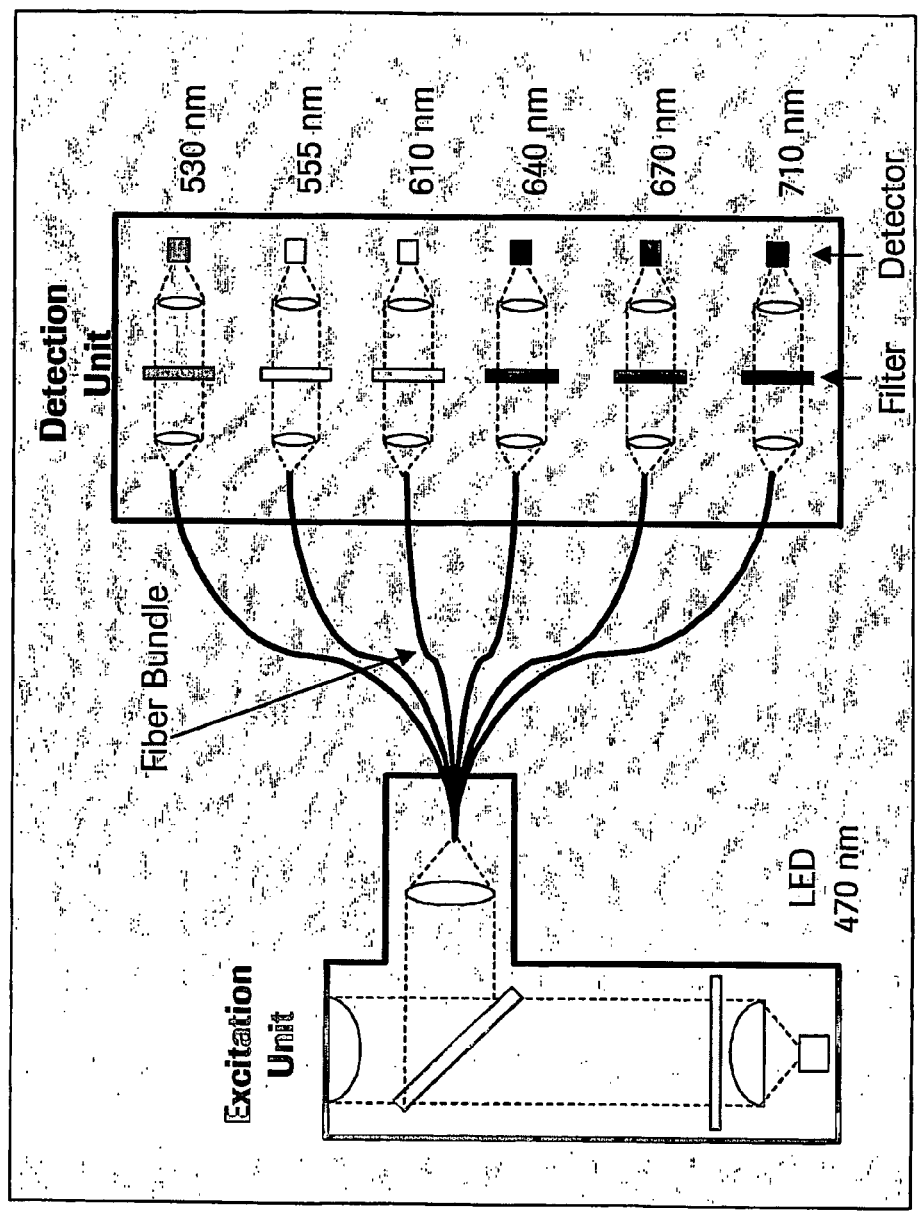
Figure 5A:
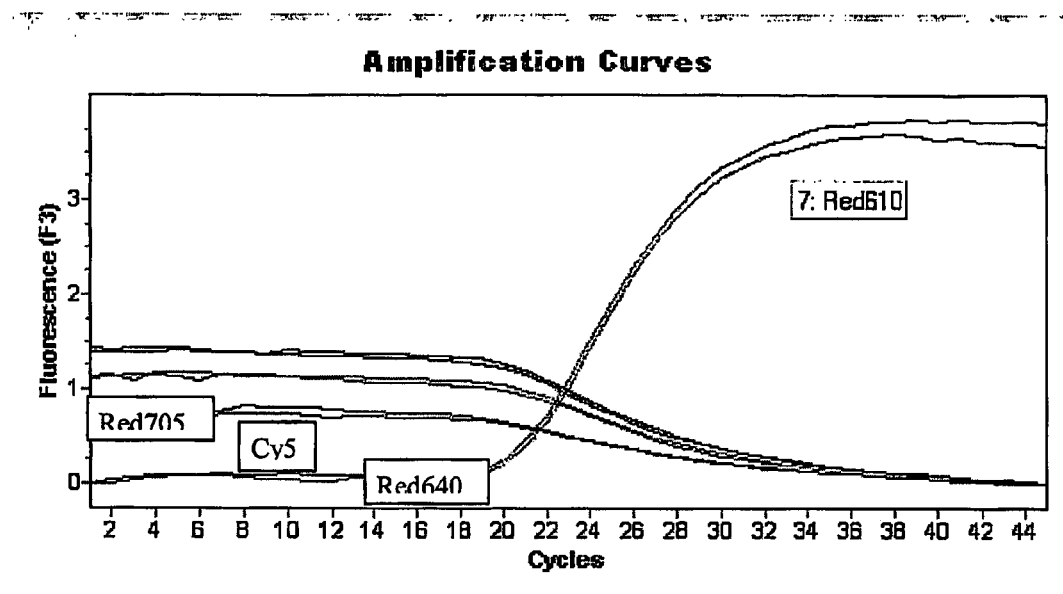
Figure 5A:
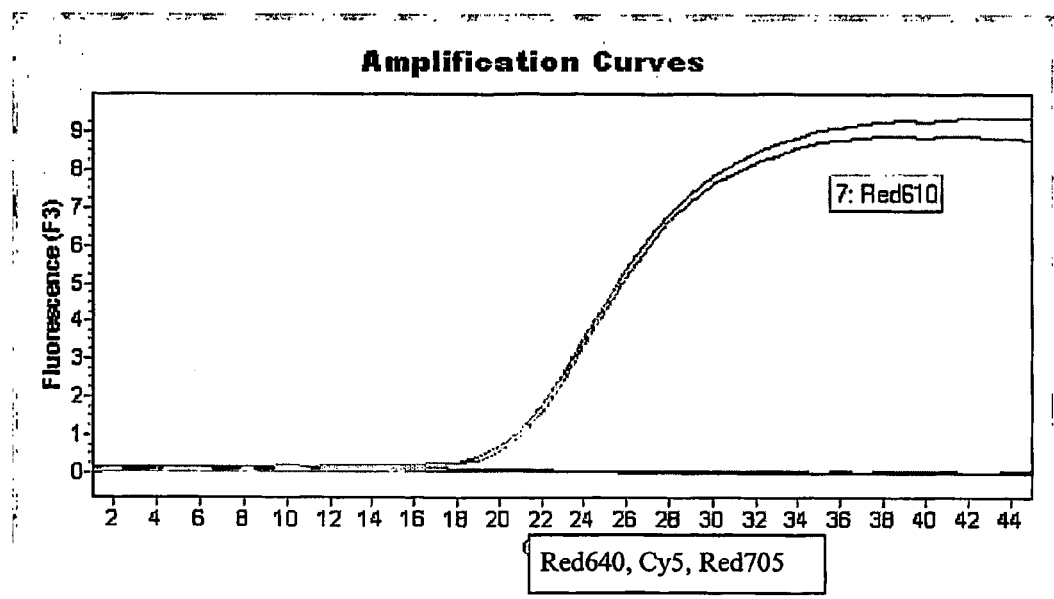
Figure 5B:
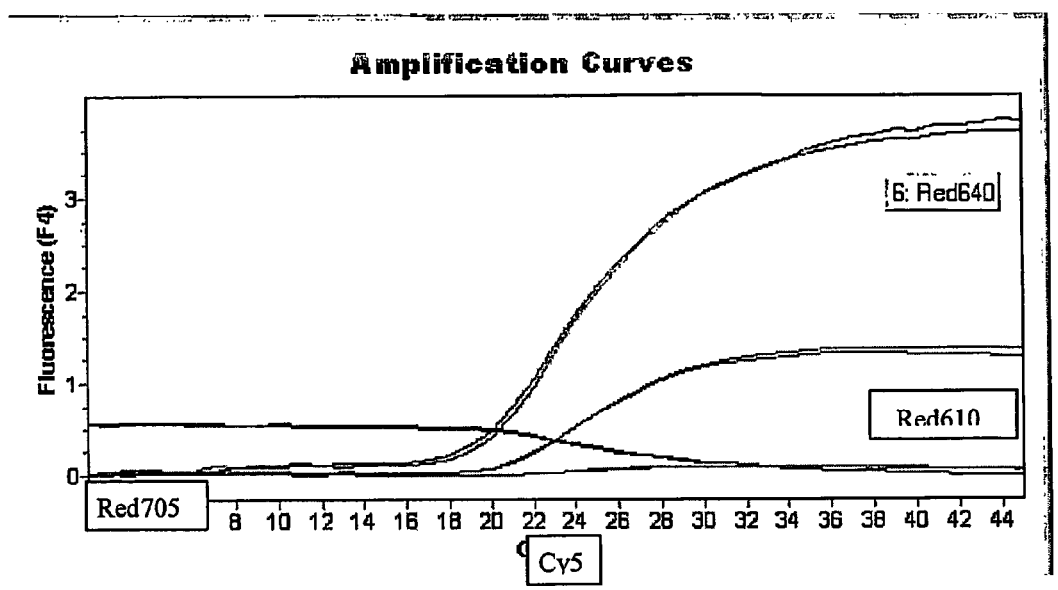
Figure 5B:
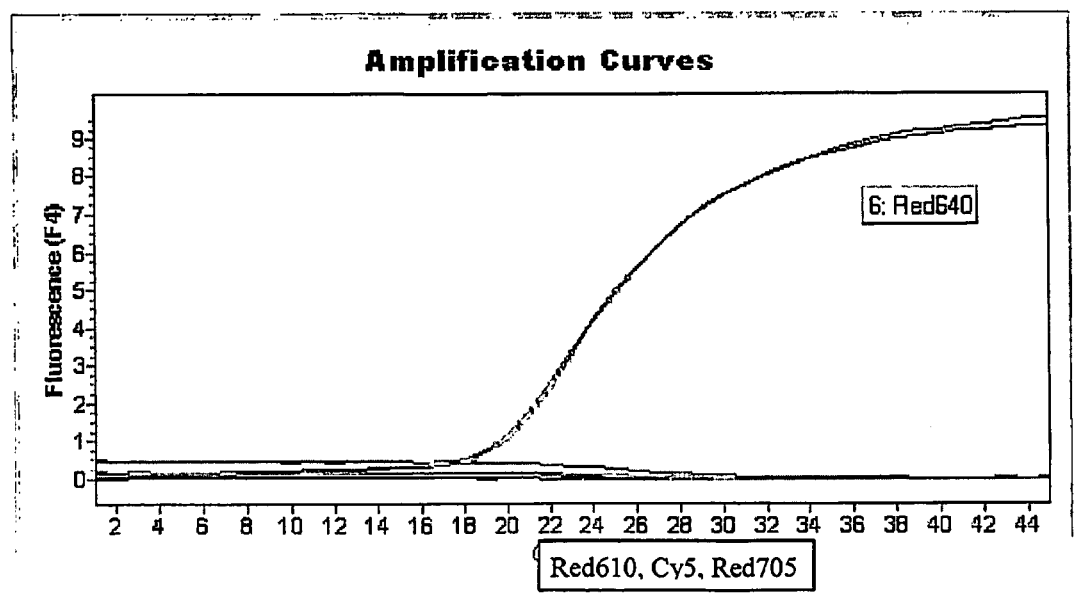
Figure 5C:
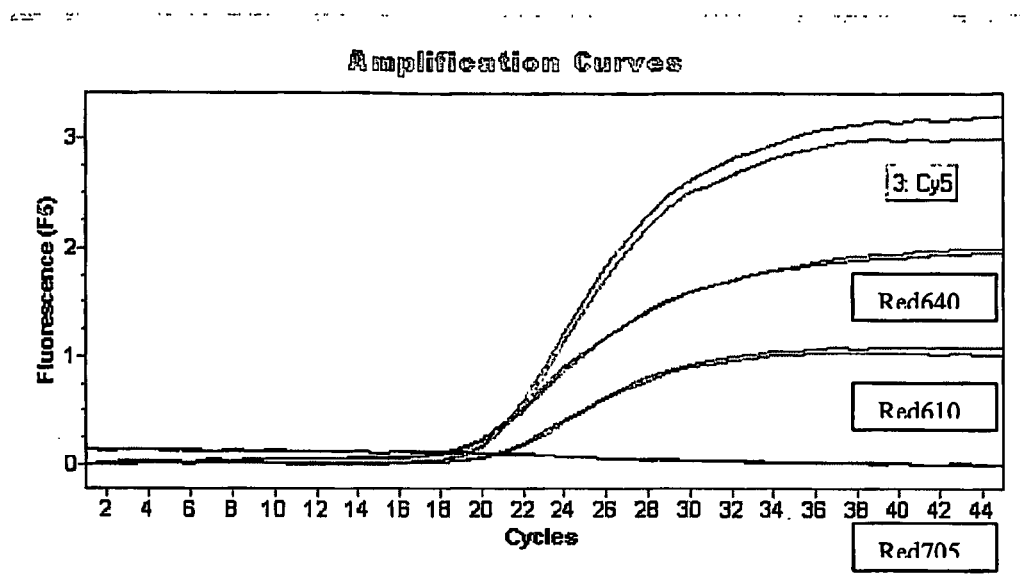
Figure 5C:
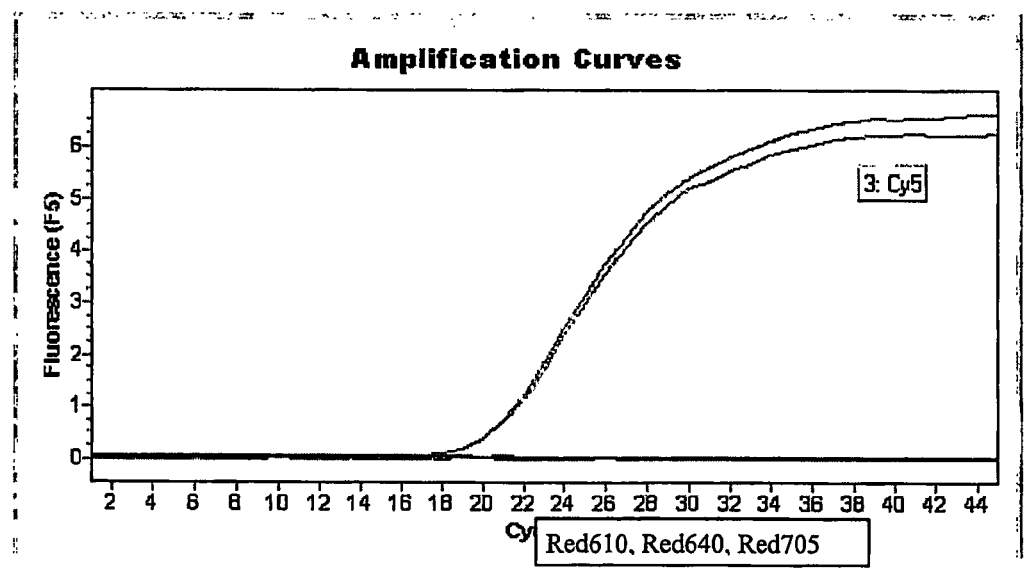
Figure 5D:
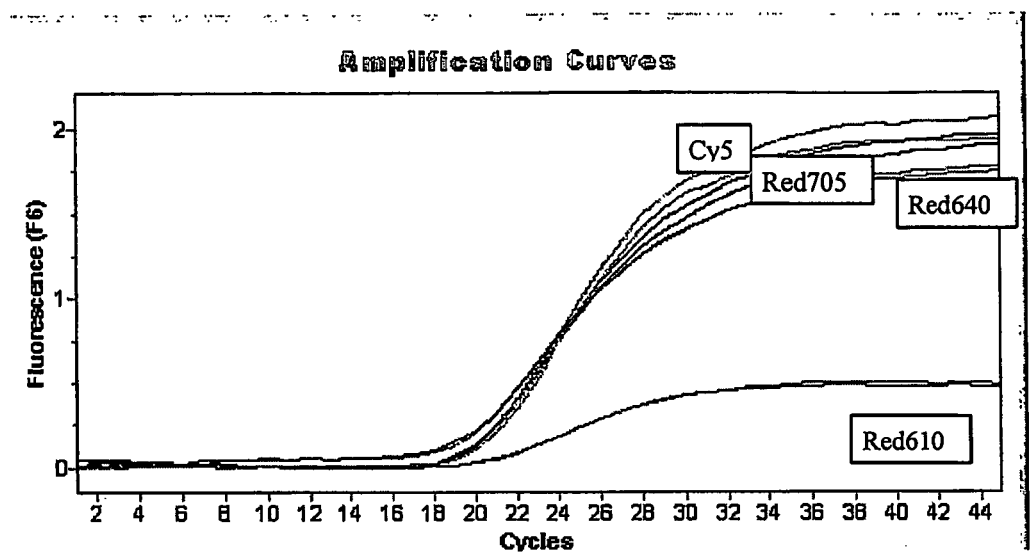
Figure 5D:
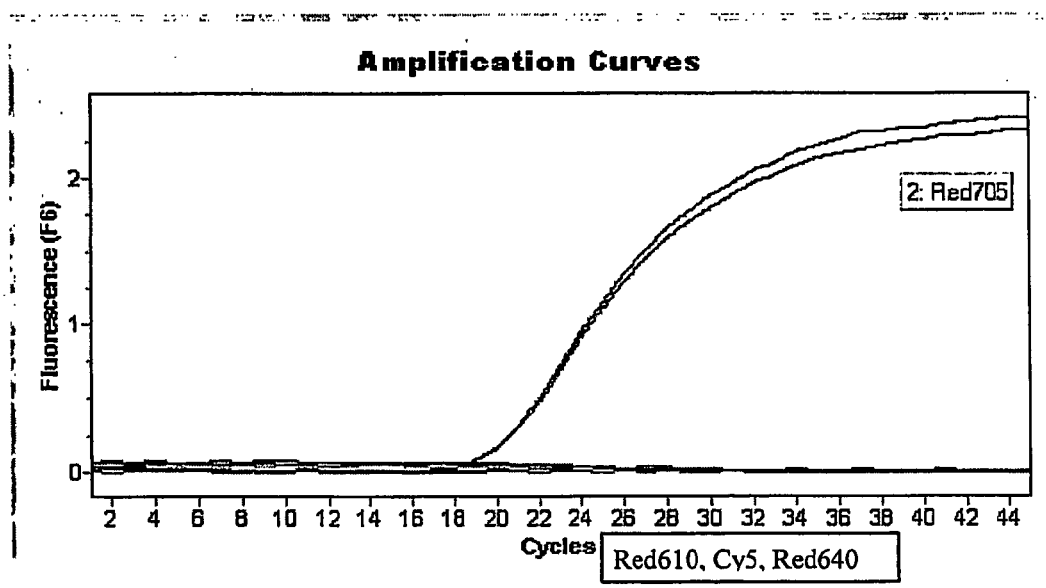
Figure 6:
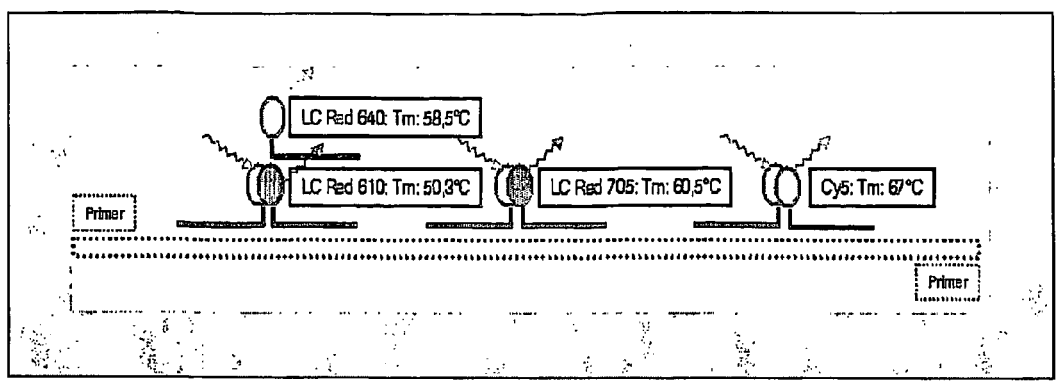
Figure 7A:
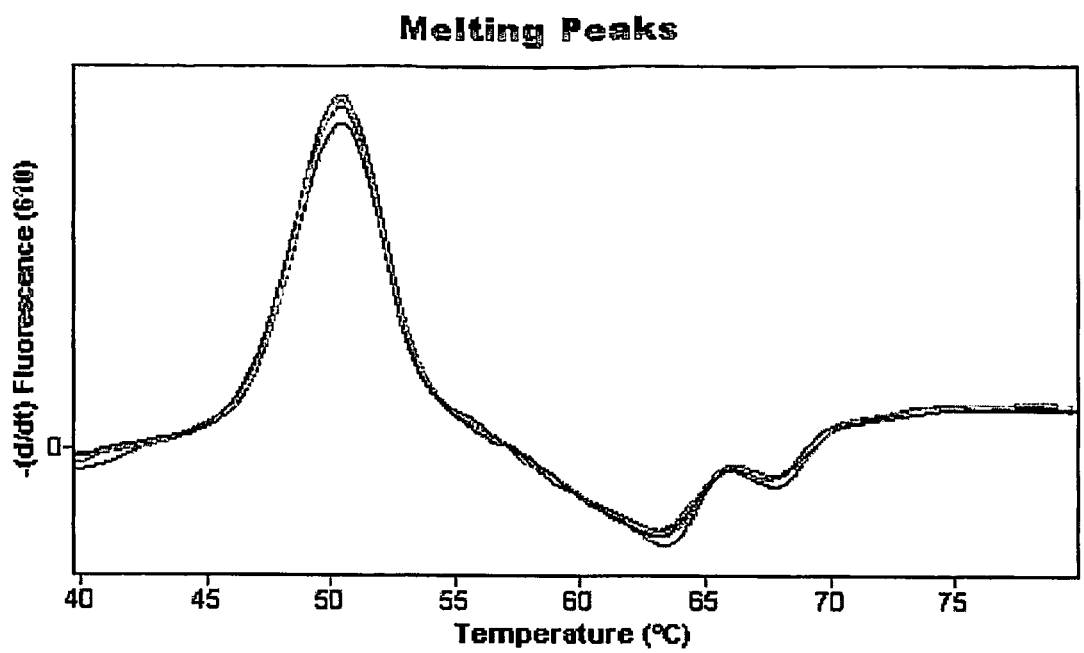
Figure 7A:
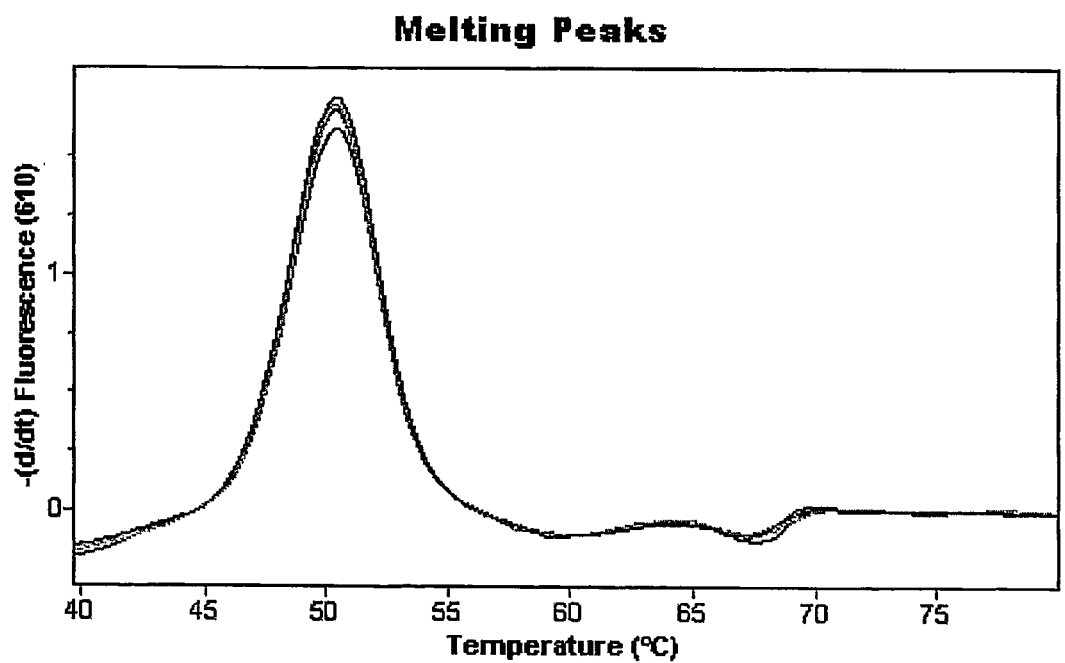
Figure 7B:
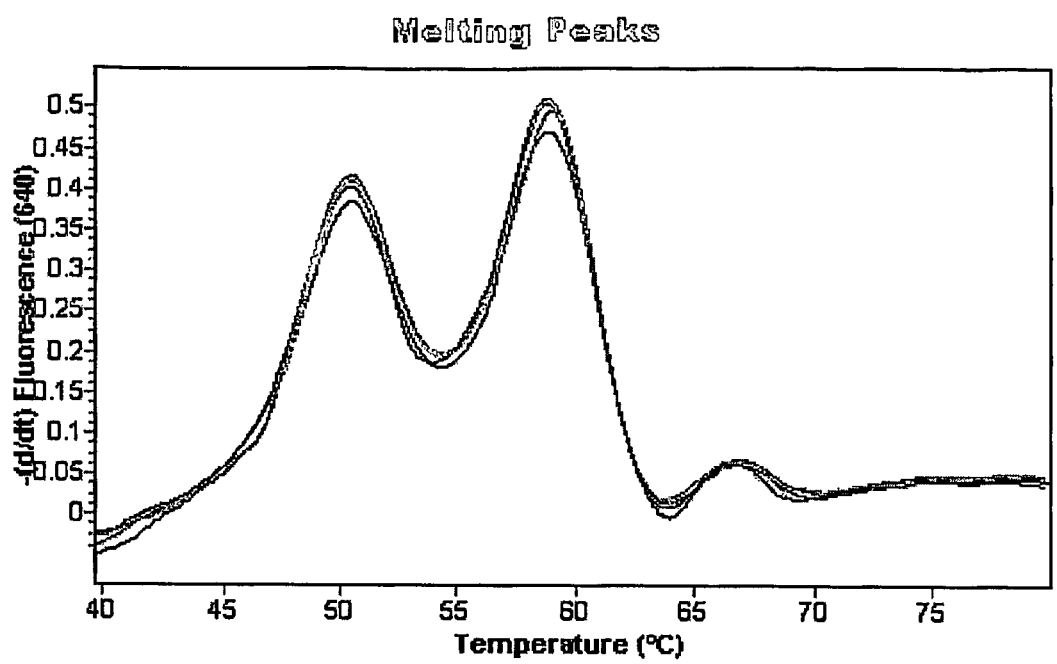
Figure 7B:
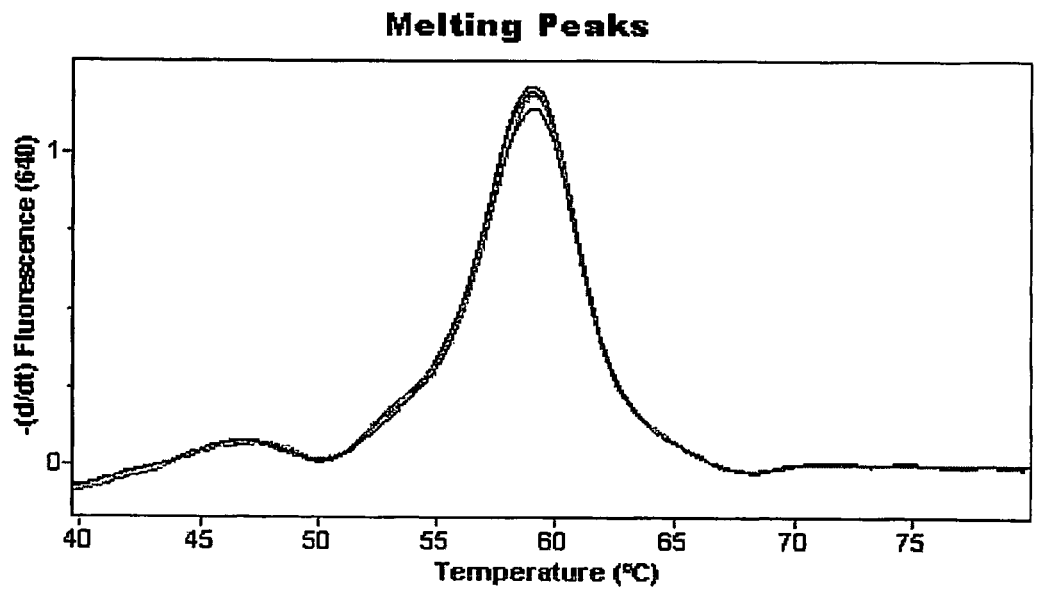
Figure 7C:
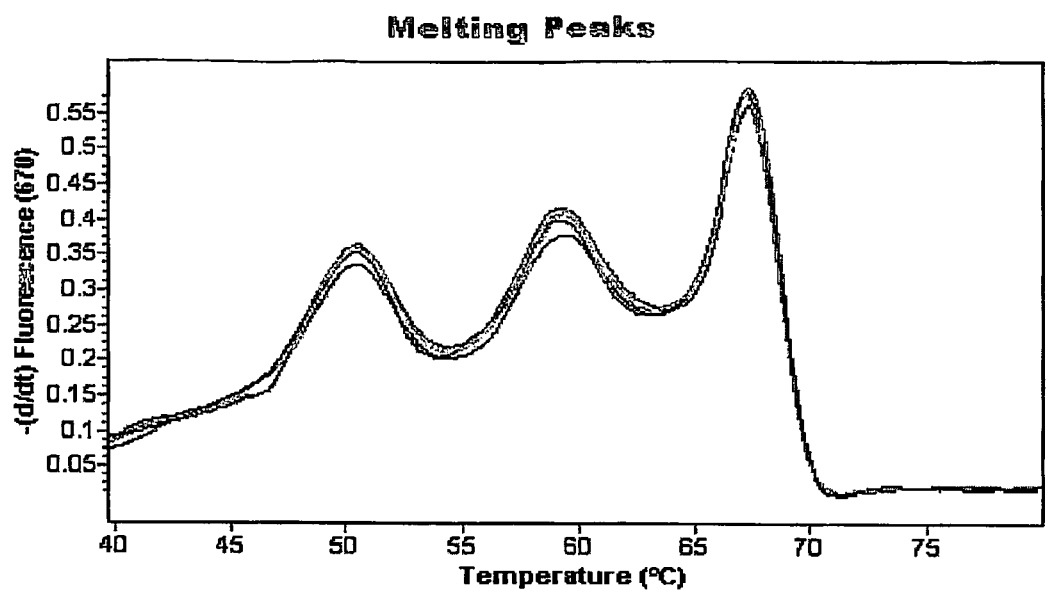
Figure 7C:
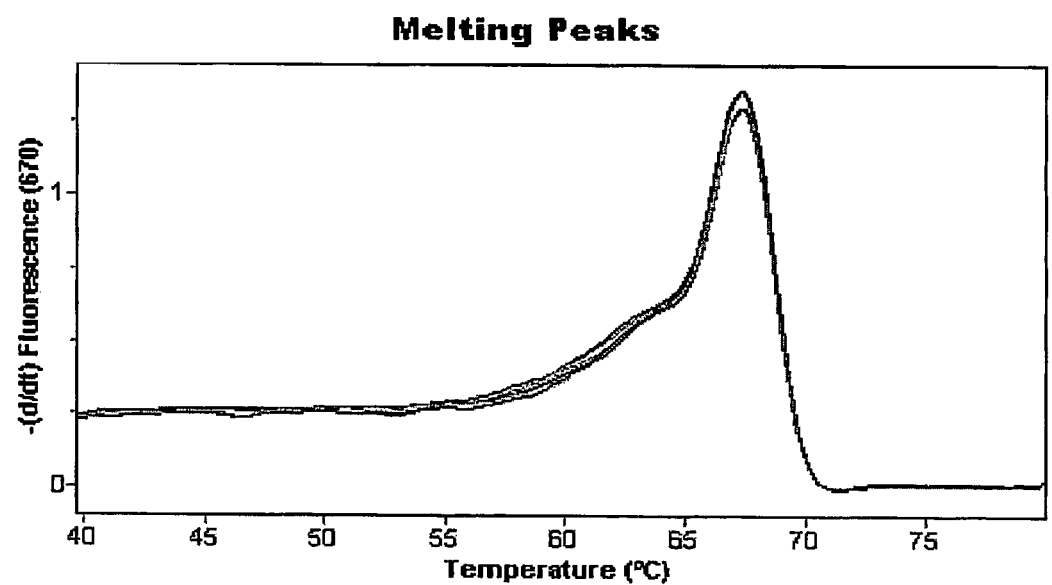
Figure 7D:
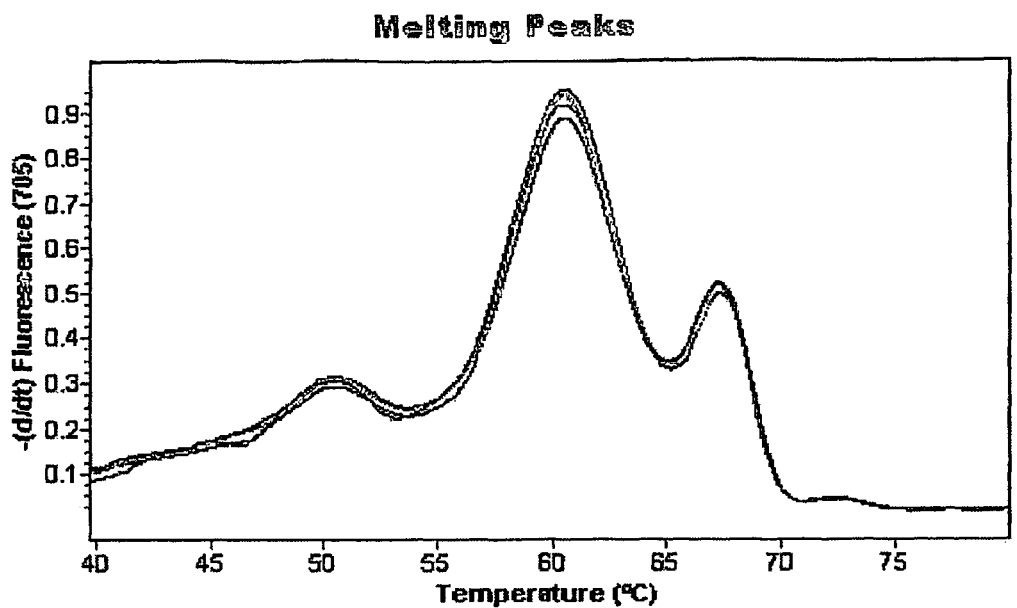
Figure 7D:
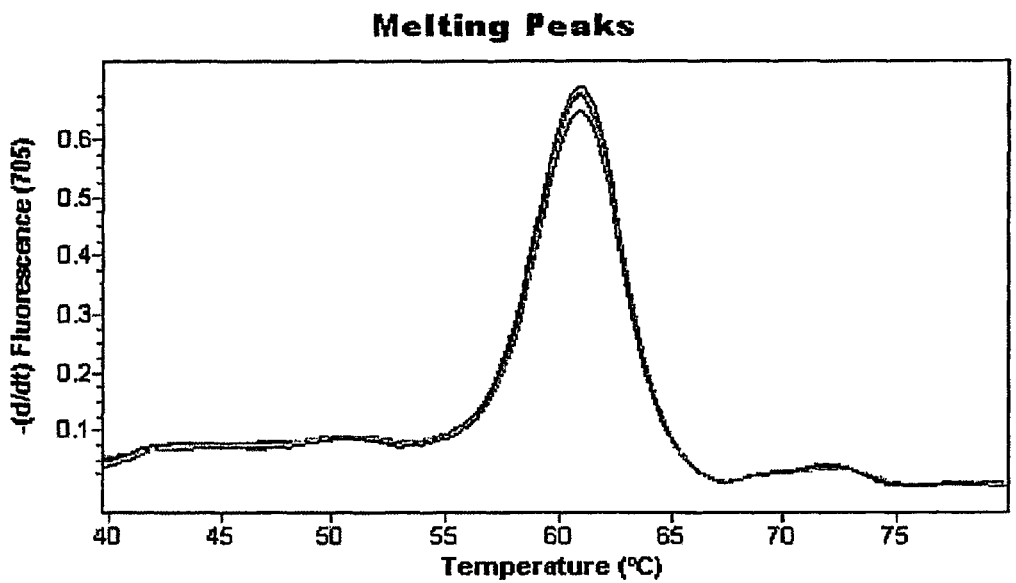
Figure 8A:
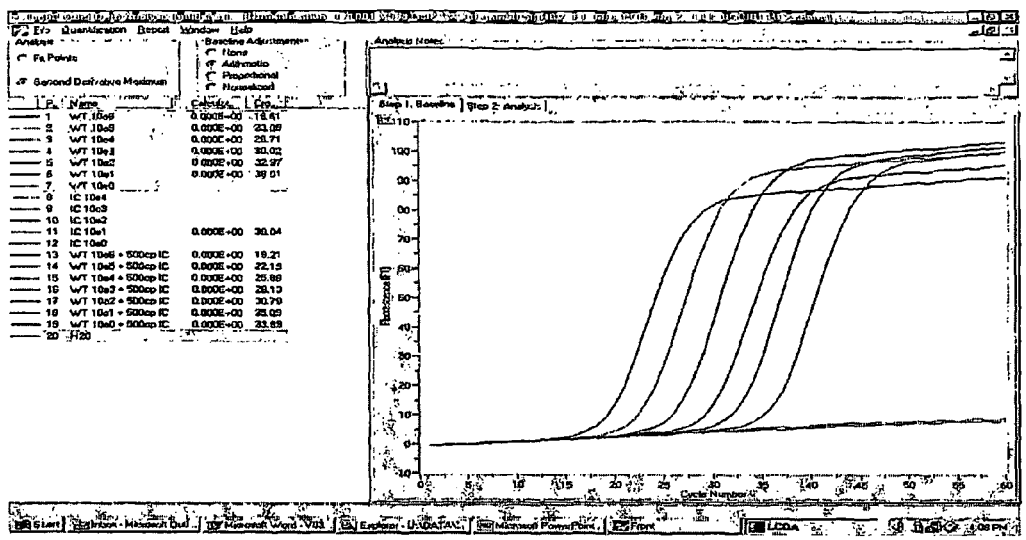
Figure 8A:
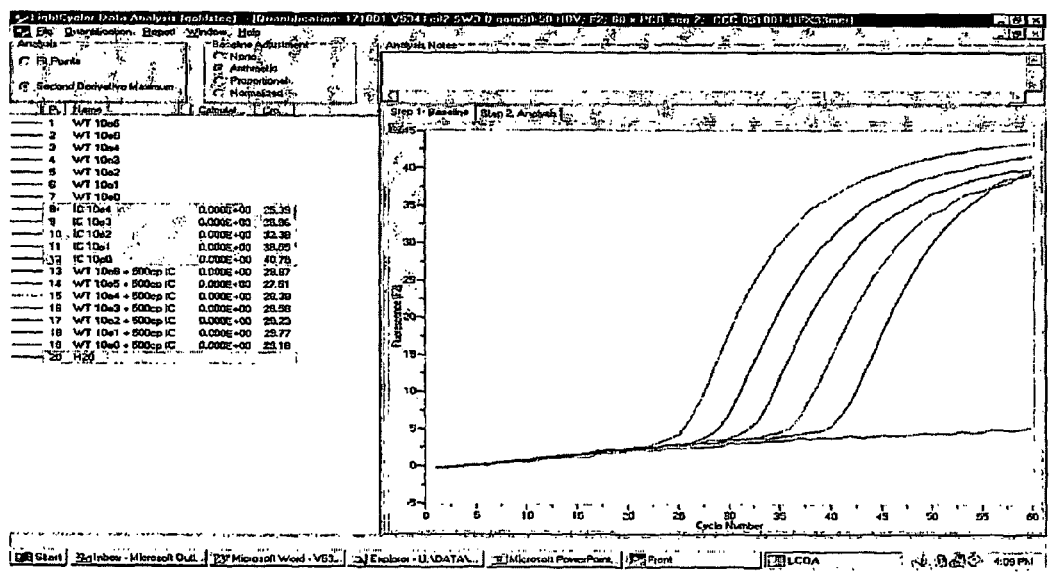
Figure 8B:
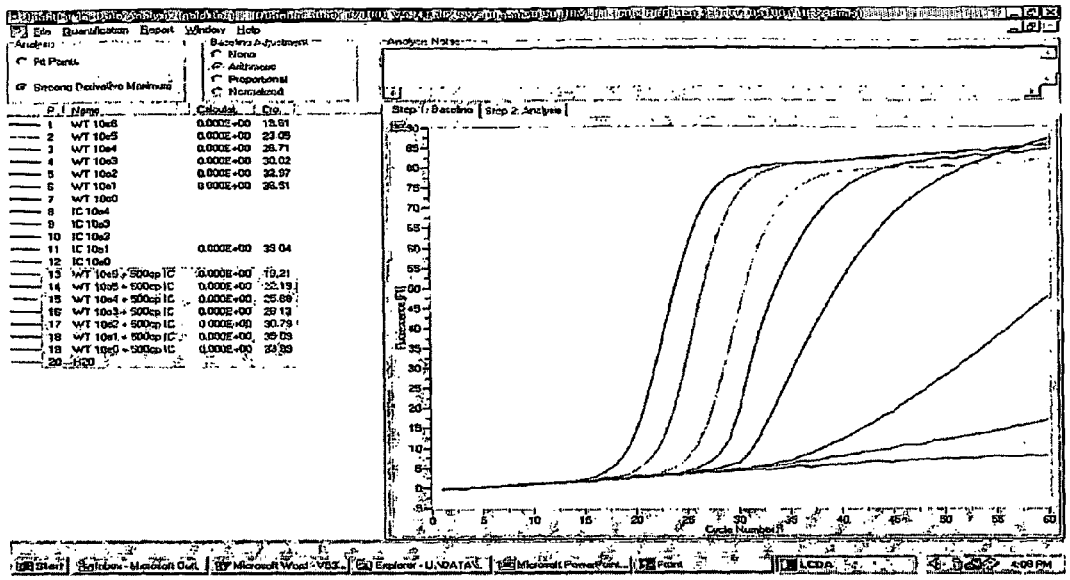
Figure 8B:
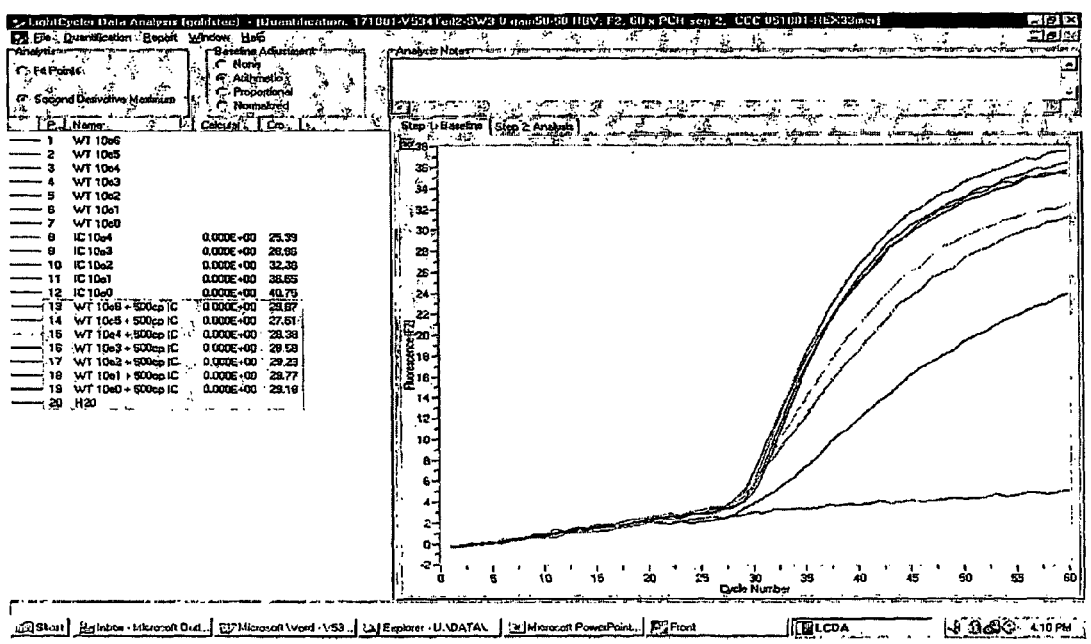

A 479 bp fragment of a specific plasmid containig a fragment of the human NAT-2 gene encoding N-Acetyl-Transsferase isozyme was amplified with specific primers and detected by fluorescence, using 4 different specific pairs of FRET Hybridization Probes. Whereas three probes were labeled at the 3'-end with Fluorescein, four detection probes were labeled 5' either with Light-Cycler-Red 610, 640, 705 or Cy5 and modified at the 3'-end by phosphorylation. A schematic drawing of this experimental set up is shown in FIG. 6. As it can be deduced from the figure, there were four differently labeled FRET acceptor probes, but only three detection sites. This resulted in a competition of annealing of two detection probes.

Assay conditions were basically the same as disclosed in example 1 with the alteration that 3×106 copies of target DNA were used.

Primer Forward:

```
5'-TGC CTT GCA TTT TCT GCT T-3'   (19mer)   (Seq. Id. No: 5)
```

Primer Reverse:

```
5'-GAG TTG GGT GAT ACA TAC A-3'   (19mer)   (Seq. Id. No: 6)
```

3'-Fluorescein HybProbe 1:

```
5'-GAA ATT CTT TGT TTG TAA TAT ACT GCT CTC TC-Fluos-3'   (32mer)   (Seq. Id. No: 7)
```

5'-Red610 HybProbe 1a:

```
5'-Red610-TGA TTT GGT CCA CGT ACC-3'   (18mer)   (Seq. Id. No: 8)
```

5'-Red640 HybProbe 1b:

```
5'-Red640-TGA TTT GGT CCA AGT ACC C-3'   (19mer)   (Seq. Id. No: 9)
```

3'-Fluorescein HybProbe 2:

```
5'-GTT GGA GAC GTC TGC AGG TAT GTA TTC ATA GAC TCA A-Fluos-3'   (37mer)  (Seq. Id. No: 10)
```

5'-Red705 HybProbe 2:

```
5'-Red705-ATC TTC AAT TGT TCG AGG TT-3'   (20mer)  (Seq. Id. No: 11)
```

3'-Fluorescein HybProbe 3:

```
5'-ATT TCC TTG GGG AGA AAT CTC GTG CCC A-Fluos-3'   (28mer)  (Seq. Id. No: 12)
```

5'-RedCy5 HybProbe 3:

```
5'-Cy5-ACC TGG TGA TGA ATC CCT TAC TAT TTA GAA TAA GGA AC-3'   (37mer)  (Seq. Id. No: 13)
```

Amplification and subsequent melting curve analysis was performed in a LightCycler instrument disclosed above as best mode of the invention according to the following thermocycling protocol:

|  | T[° C.] | t[sec] | Ramp-rate [° C./sec] | Acquisition | Cycles |
|---|---|---|---|---|---|
| Denaturation | 95 | 600 | 20.0 | none | 1 |
| Amplification | 95 | 10 | 20.0 | none | |
|  | 55 | 10 | 20.0 | single | 45 |
|  | 72 | 20 | 3.0 | none | |
| Melting Curve | 95 | 60 | 20.0 | none | |
|  | 40 | 60 | 20.0 | none | 1 |
|  | 80 | 0 | 0.1 | cont | |
| Cooling | 40 | 30 | 20.0 | none | 1 |

Results are shown in FIG. 7. As it can be deduced from the figure, 4 color melting curve analysis using Hybridization Probes with the 4 different acceptor dyes could be performed using an approriate color compensation method. Hybridization Probe specific melting peaks could then be detected without any substantial crosstalk effects.

EXAMPLE 3

Dual Color TaqMan Detection

A LightCycler instrument according to the best mode of the invention provided all means for sensitive detection of dual color TaqMan assays. The established TaqMan dye FAM and HEXs were well excited with the 470 nm LED and after using the instrument's color compensation function could differentially be identified in the 530 nm and 560 nm detection channels with high sensitivity. Transfer of dual color TaqMan assay protocols to the instrument according to the invention was simply performed by supplementing established assay conditions with BSA.

Different examples of successful dual color amplification and detection are shown in FIG. 8. FIG. 8a shows that in mono-color experiments using either FAM or HEX, a detection sensitivity of about 1 copy/µl for dual color TaqMan assays was obtained. (Only negative controls did not result in a significant increase in fluorescence after the PCR reaction). FIG. 8b shows a dual color experiment, wherein a Hex labeled TaqMan probe was always used to detect 500 copies of a first target DNA and in the same reaction a FAM labeled TaqMan probe was used to detect different amounts ($10^0$-$10^6$ copies) of a second target DNA.

The dynamic range (being indicative for the relative difference in concentrations of the two targets to become detected) was about $10^3$.

List of References

Bernard, P. S., et al., Analytical Biochemistry 255 (1998) 101-107

EP 0 640 828

EP 0747447

Higuchi R, C Fockler G Dollinger and R Watson, Kinetic PCR analysis: real time monitoring of DNA amplification reactions, Bio/Technology 11 (1993) 1026-1030

Higuchi R, G Dollinger, P S Walsh and R. Griffith, Simultaneous amplification and detection of specific DNA sequences, Bio/Technology 10 (1992) 413-417

Matthews, J. A., and Kricka, L. J., Analytical Biochemistry 169 (1988) 1-25

Pedersen, S., Bioradiations 107 (2001) 10-11

Review: Resonance Energy Transfer Editors: Meer, B Wieb van der et al., VCH Publishers INC., 1994

U.S. Pat. No. 5,118,801

U.S. Pat. No. 5,538,848

U.S. Pat. No. 5,750,409

U.S. Pat. No. 6,015,674

U.S. Pat. No. 6,174,670

U.S. Pat. No. 6,197,520

U.S. Pat. No. 6,369,893

WO 02/14555

WO 97/46707

WO 97/46712

WO 98/46714

The invention claimed is:

1. A real time PCR instrument comprising:
   an excitation unit comprising:
   a plurality of reaction vessels for containing a reaction mixture;
   exactly one monochromatic light source, wherein the monochromatic light source is an LED emitting at 470 nm; and
   a lightpipe arranged to receive light from the reaction vessels and distributing said light into a six-leg optical fiber bundles of 50 μm single glass fibers;
   a detection unit comprising six separate fluorescent detector entities, each of said detector entities having a central detection wavelengths at 530 nm, 555 nm, 610 nm, 640 nm, 670 nm, and 710 nm +/−5 nm respectively, wherein the excitation unit and the detection unit are mechanically decoupled and connected by the six-leg optical fiber bundles where each bundle transmits light into each of the six detector entities; and
   means for heating and cooling;
   wherein the detector entities simultaneously detect maximum fluorescence emission of at least four differently labeled FRET hybridization probe pairs, simultaneously detect maximum fluorescence emission of at least two differently labeled TaqMan hybridization probes, and detect maximum fluorescence emission of SybrGreenI.

2. A real time PCR instrument according to claim 1 wherein the reaction vessels comprise capillaries.

3. A real time PCR instrument according to claim 2, wherein the capillaries are capillaries having an outer diameter of less than 5 mm.

4. A real time PCR instrument according to claim 1, wherein each of said detector entities have a central detection wavelengths at 530 nm, 555 nm, 610 nm, 640 nm, 670 nm, and 710 nm +/−2 nm respectively.

* * * * *

UNITED STATES PATENT AND TRADEMARK OFFICE
CERTIFICATE OF CORRECTION

| | | |
|---|---|---|
| PATENT NO. | : 8,137,616 B2 | Page 1 of 1 |
| APPLICATION NO. | : 10/549648 | |
| DATED | : March 20, 2012 | |
| INVENTOR(S) | : Gregor Sagner et al. | |

It is certified that error appears in the above-identified patent and that said Letters Patent is hereby corrected as shown below:

On the Title Page

(73) Assignee should read: Roche Diagnostics Operations
　　　　　　　　　　　　　　　Indianapolis, IN (US)

Signed and Sealed this
Second Day of October, 2012

David J. Kappos
*Director of the United States Patent and Trademark Office*